(12) United States Patent
Park

(10) Patent No.: US 8,257,960 B2
(45) Date of Patent: Sep. 4, 2012

(54) SACCHAROMYCES MICROORGANISMS HAVING ODOR CONTROL ACTIVITY AND USES THEREOF

(76) Inventor: Se-Joon Park, Seoul (KR)

( * ) Notice: Subject to any disclaimer, the term of this patent is extended or adjusted under 35 U.S.C. 154(b) by 1084 days.

(21) Appl. No.: 12/083,762

(22) PCT Filed: Oct. 19, 2006

(86) PCT No.: PCT/KR2006/004270
§ 371 (c)(1),
(2), (4) Date: Apr. 17, 2008

(87) PCT Pub. No.: WO2007/046650
PCT Pub. Date: Apr. 26, 2007

(65) Prior Publication Data
US 2009/0208470 A1 Aug. 20, 2009

(30) Foreign Application Priority Data

| Oct. 22, 2005 | (KR) | 10-2005-0099940 |
| Nov. 1, 2005 | (KR) | 10-2005-0103923 |
| Sep. 26, 2006 | (KR) | 10-2006-0093709 |
| Sep. 26, 2006 | (KR) | 10-2006-0093713 |
| Sep. 26, 2006 | (KR) | 10-2006-0093724 |
| Sep. 28, 2006 | (KR) | 10-2006-0094687 |
| Sep. 28, 2006 | (KR) | 10-2006-0094706 |
| Oct. 10, 2006 | (KR) | 10-2006-0098303 |

(51) Int. Cl.
*C12N 1/20* (2006.01)
(52) U.S. Cl. ........ 435/255.2; 424/93.51; 426/62
(58) Field of Classification Search .......... None
See application file for complete search history.

(56) References Cited

U.S. PATENT DOCUMENTS

| 6,051,219 A | 4/2000 | Kubota |
| 6,403,128 B2 * | 6/2002 | Ueda et al. .......... 426/18 |
| 6,489,158 B1 * | 12/2002 | Hendrick et al. ........ 435/255.2 |
| 6,649,397 B1 | 11/2003 | Nakamura |
| 7,101,544 B1 * | 9/2006 | Sawada et al. ......... 424/93.51 |

FOREIGN PATENT DOCUMENTS

| KR | 10-1997-0043015 | 7/1997 |
| KR | 10-1998-056781 | 9/1998 |
| KR | 1020010054459 | 7/2001 |
| KR | 1020010091766 | 10/2001 |
| KR | 1020020027818 A | 4/2002 |
| KR | 1020020084347 | 11/2002 |
| KR | 2020040029619 | 12/2004 |
| KR | 100466580 | 1/2005 |

OTHER PUBLICATIONS http://www.atcc.org/ATCCAdvancedCatalogSearch/tabid/112/Default.aspx, accessed Nov. 14, 2011.*
Vital et al, Brazilian Journal of Microbiology (2002) 33:230-235.*

* cited by examiner

*Primary Examiner* — Irene Marx
(74) *Attorney, Agent, or Firm* — Edwards Wildman Palmer LLP

(57) ABSTRACT

The present invention relates to novel microorganisms having the efficiency of removing an offensive odor from organic waste and the use thereof. More particularly, the novel microorganisms have the effects of preventing or removing the offensive odor from organic waste, killing insects and fungi, preventing decomposition, and promoting digestion and fermentation. The inventive microorganisms have the effects of preventing or removing the offensive odor from organic waste and killing noxious insects and plant pathogenic fungi, can be used as feed additives and antibiotic substitutes, and also are useful for the preparation of fermented healthy foods.

10 Claims, 6 Drawing Sheets

FIG. 1
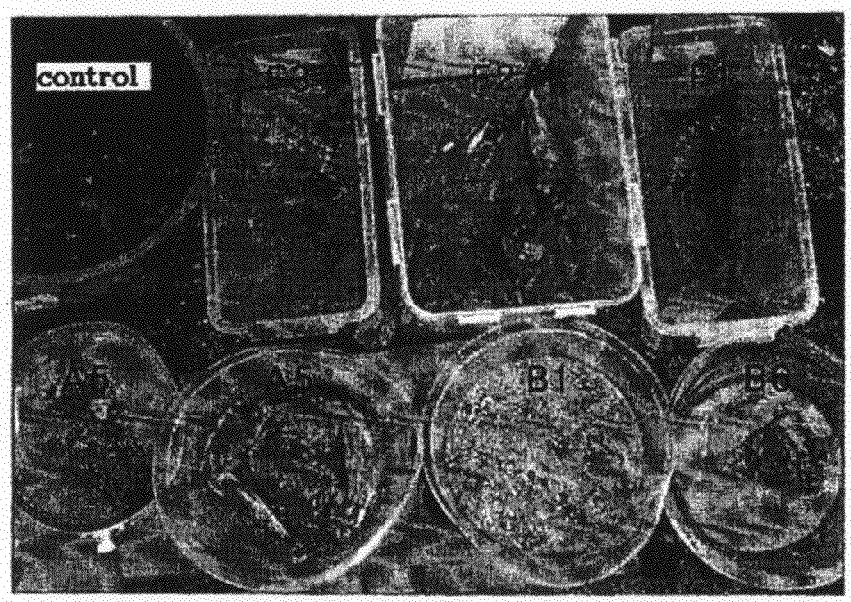
A
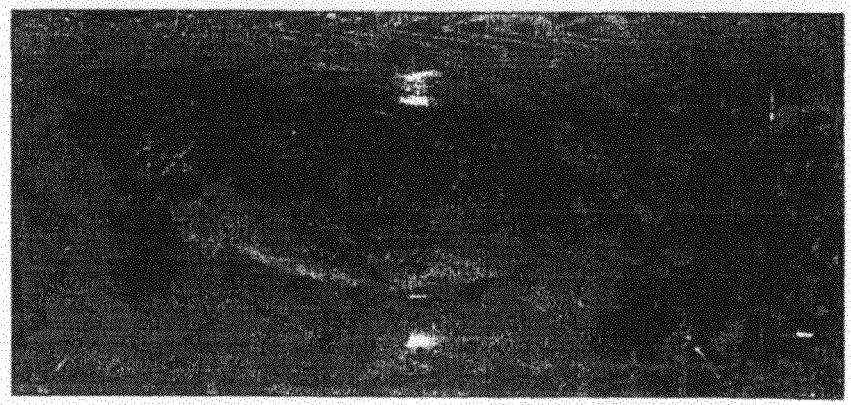
B

FIG. 3
A
B
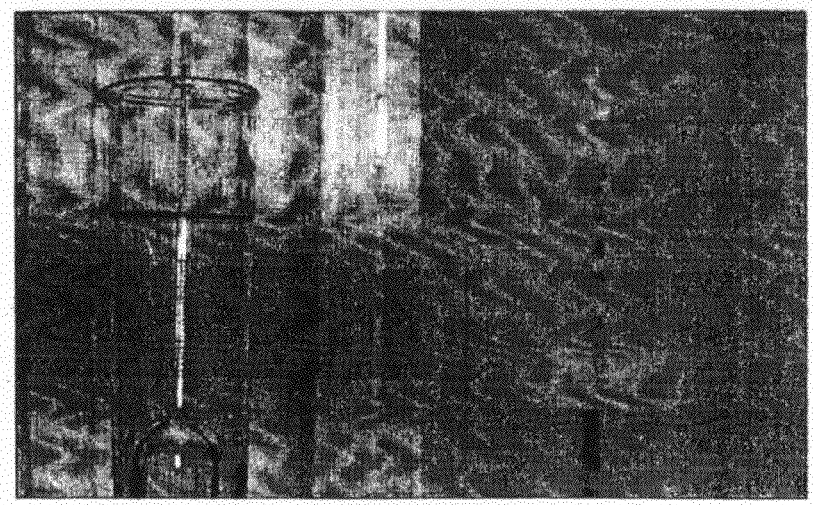

FIG. 4
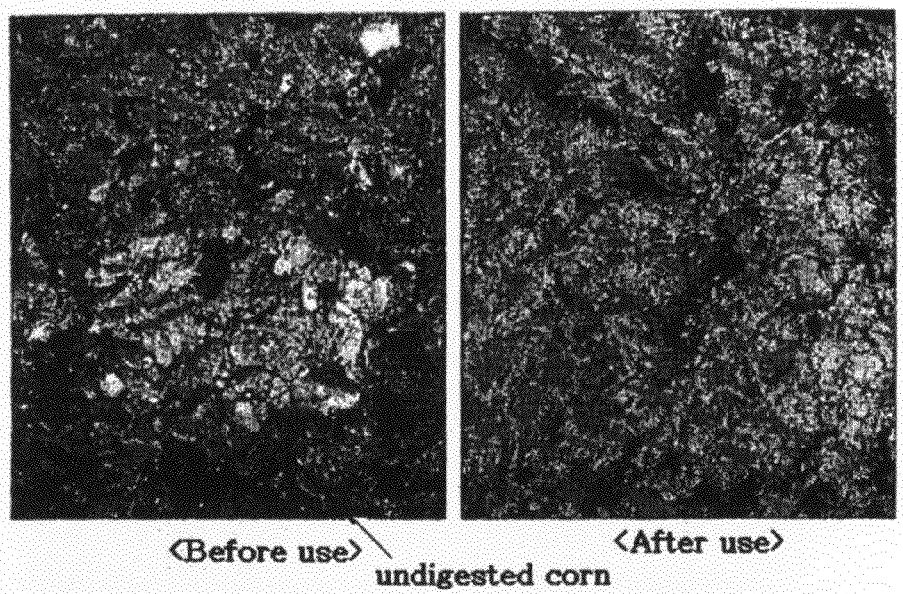
⟨Before use⟩ undigested corn ⟨After use⟩
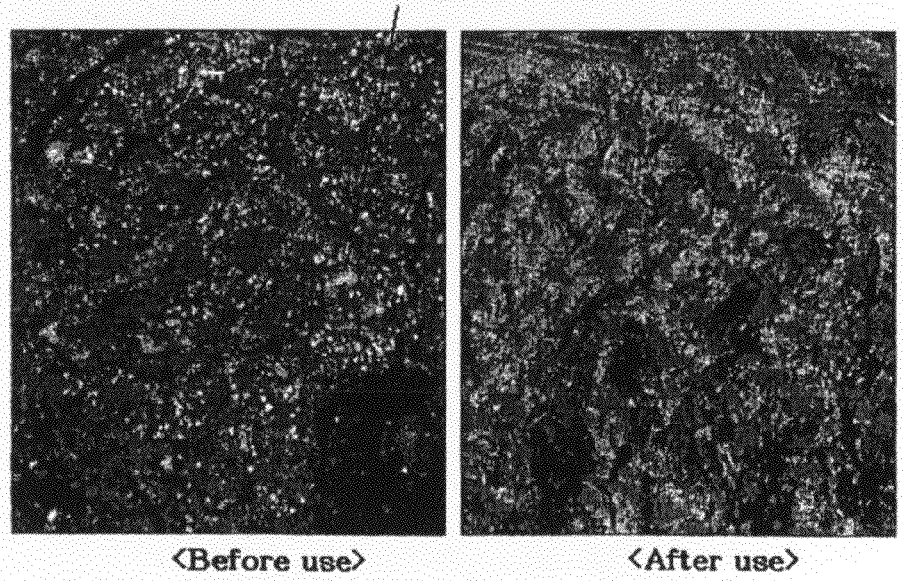
⟨Before use⟩ ⟨After use⟩

FIG. 6
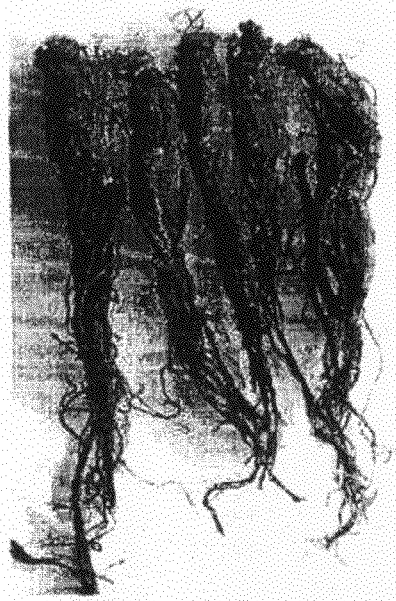
primary fermentation
secondary fermentation
tertiary fermentation
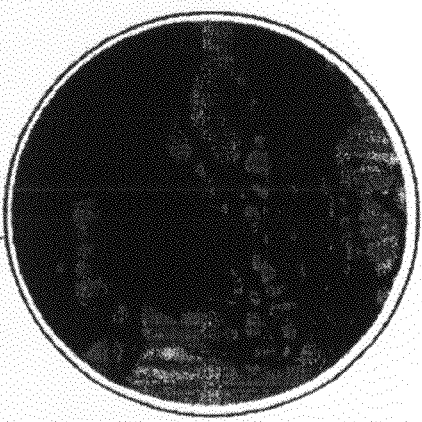
tertiary fermentated root

SACCHAROMYCES MICROORGANISMS HAVING ODOR CONTROL ACTIVITY AND USES THEREOF

TECHNICAL FIELD

The present invention relates to novel microorganisms having the effect of removing an offensive odor from organic waste and the use thereof, and more particularly to microorganisms having the functions of preventing or removing the offensive odor of organic waste, killing insects and fungi, preventing decomposition, and promoting digestion and fermentation; and the use thereof.

BACKGROUND ART

Sewage wastewater and waste, which are inevitable consequence of human life, and organic waste such as livestock manure generated from animals or livestock, are biochemically degraded by the action of minerals, metals, salts and microorganisms in the soil under suitable humidity and temperature, thus causing various odors. The generated odors are hydrogen sulfide, carbolic acids or compounds thereof, and other irritating gaseous substances, which give unpleasant sensations in daily life, and among them, inorganic substances and alkaline substances are substantially odorless, but almost all the organic substances generate odors. Particularly, sulfide compounds and nitrogen compounds are the main causes of odors.

Prior methods of removing the odors thus generated include a masking method, an adsorption method, a neutralization method, sterilization method and the like. The masking method is a method of generating a distinctive smell stronger than an offensive odor, such that the offensive odor is not felt, but this method requires expensive fragrances and it is difficult to fundamentally remove the offensive odor. The adsorption method is a physical method of adsorbing an offensive odor onto activated carbon or the like while discharging the offensive odor to the outdoors by an exhaust system, and has shortcomings in that high construction cost is required and high maintenance cost is incurred because expensive activated carbon must be periodically used. Also, the neutralization method is a chemical method of neutralizing an offensive odor into an acidic or alkaline substance, and enables an offensive odor to temporarily disappear during the use thereof. However, the neutralization method has shortcomings in that the disappearance of the offensive odor does not last long, it is difficult to treat an odor-causing substance having both acidic and basic groups, and it cannot have any effect if an odor-causing substance is neutral. The sterilization method is a method of killing bacteria themselves degrading organic substances, so as to prevent the decomposition of the organic substances and the generation of odors from the organic substances, and has a shortcoming in that it requires an expensive bactericide or preservative for maintaining an odorless state for a long time. Particularly, because the sterilization method aims to prevent the decomposition or fermentation of organic substances from occurring, it cannot be used in cases where a desired substance is obtained only by odors that are caused by the decomposition or fermentation of organic waste.

Thus, it will be preferable in economic terms to use a biological method of oxidizing and decomposing organic waster using microorganisms such as bacteria.

In Korean Patent Registration Nos. 10-0536456 and 10-0581738, a novel yeast strain and the genus *Bacillus* strain that ferment organic waste were isolated and identified and these strains were confirmed to have the effects of preventing offensive odors and killing and inhibiting harmful insects and pathogenic bacteria. Also, most fermented foods, including alcoholic drinks, breads, vinegars, fermented soybean foods (soy sauce, soybean paste, thick soypaste mixed with red peppers, etc.), fermented milk products (cheese, butter, yoghurt, etc.), salted foods (Kimchi, salted fish, etc.), red ginseng, and skates, are made by a number of microorganisms produced in nature and have characteristic odors. Recently, as interest in fermentation has increased, various studies, including the preparation of fermented ginseng, Chungkookjang confectionary and lactic acid fermented foods, the characteristic odors of which were removed, have been conducted.

Accordingly, the present inventors have made extensive efforts to develop a method for removing an offensive odor from organic waste using microorganisms. As a result, the present inventors have isolated and identified novel microorganisms having the efficiency in removing the offensive odor of organic waste and found that the novel microorganisms show the effects of removing the offensive odor of organic waste, killing insects and fungi, preventing decomposition, and promoting fermentation, thereby completing the present invention.

SUMMARY OF INVENTION

It is an object of the present invention to provide microorganisms having the efficiency in removing an offensive odor from organic waste.

Another object of the present invention is to provide a microbial agent for the fermentation of organic waste, which contains said microorganisms.

Still another object of the present invention is to provide an agent for preventing or removing an offensive odor from organic waste, which contains said microorganisms.

Yet another object of the present invention is to provide an insecticide, a microbicide and a preservative, which contain said microorganisms.

Yet still another object of the present invention is to provide a feed additive and a probiotic agent, which contain said microorganisms.

Still further object of the present invention is to provide a method for preparing a fermented food, which comprises fermenting food using said microorganisms and a fermented food prepared by said method.

To achieve the above objects, in one aspect, the present invention provides a microorganism selected from the group consisting of *Saccharomyces exiquus* SJP6728AF1 (KCCM-10675P), *Saccharomyces exiquus* SJP6729AF2(KCCM-10677P), *Candida fructus* SJP6730AF3 (KCCM-10679P), *Candida zeylanoides*SJP6840AF4 (KCCM-10695P), *Kazachstania aerobia* SJP6844AF5 (KCCM-10696P), *Candida humilis* SJP6726AF6 (KCCM-10697P), *Candida zeylanoides*SJP6843AF7(KCCM-10698P), *Lactobacillu paraplantarum* SJP66722A5 (KCCM-10676P), *Bacillus badius* SJP6731B31 (KCCM-10680P), *Paenibacillus lactis* SJP6732B2 (KCCM-10726P), *Paenibacillus sp.* AY397772 SJP6719B3 (KCCM-10727P), *Brevibacillus borstelensis*SJP6734B4 (KCCM-10728P), *Paenibacillus polymyxa* SJP6735B6 (KCCM-10678P), *Lactobacillus casei* SJP6841L2 (KCCM-10729P), *Lactobacillus brevis* SJP6720L3 (KCCM-10730P), *Leuconostoc citreum* SJP6723L4 (KCCM-10731P) and *Carnobacterium maltaromaticum* SJP6742L5 (KCCM-10732P).

In another aspect, the present invention provides a microbial agent for the fermentation of organic waste, which contains one or more microorganisms selected from the group consisting of said microorganisms.

In still further aspect, the present invention provides an agent for preventing or removing an offensive odor from organic waste, which contains one or more microorganisms selected from the group consisting of said microorganisms.

In yet further aspect, the present invention provides an insecticide, a microbicide and a preservative, which contains one or more microorganisms selected from the group consisting of said microorganisms.

In yet still another aspect, the present invention provides a feed additive or a probiotic agent, which contains one or more microorganisms selected from the group consisting of said microorganisms.

In still further aspect, the present invention provides a method for preparing a fermented food, the method comprises fermenting food using one or more microorganisms selected from the group consisting of said microorganisms, as well as a fermented food prepared through said method.

Other features and embodiments of the present invention will be more fully understood from following detailed description and the appended claims.

BRIEF DESCRIPTION OF DRAWINGS

FIG. 1 shows the insecticidal effect of the inventive microorganisms against fly larvae. In FIG. 1, A illustrates photographs showing the insecticidal effects of the inventive microorganisms against six kinds of fly larvae, and B is a photograph enabling observation of the state of a fish left to stand for 3 days in an insecticidal test against said fly larvae.

FIG. 3 illustrates photographs showing the measurement of the alcohol-fermenting ability of the microorganisms according to the present invention. In FIG. 3, A is a photograph showing a distillation method for the measurement of alcohol in food wastewater treated with the microorganisms according to the present invention, and B is a photograph showing the measurement of the specific gravity of distilled water generated in said measurement A.

FIG. 4 illustrates photographs of manures from livestock fed with feed containing the microorganisms according to the present invention. In FIG. 4, A is a photograph of manure from livestock fed with feed containing an SJP6728AF1 culture broth. B is a photograph of manure from livestock fed with feed containing an SJP6729AF2 culture broth.

FIG. 6 shows photographs of ginseng fermented using the microorganisms according to the present invention.

DETAILED DESCRIPTION OF THE INVENTION AND PREFERRED EMBODIMENTS

Figure 2:
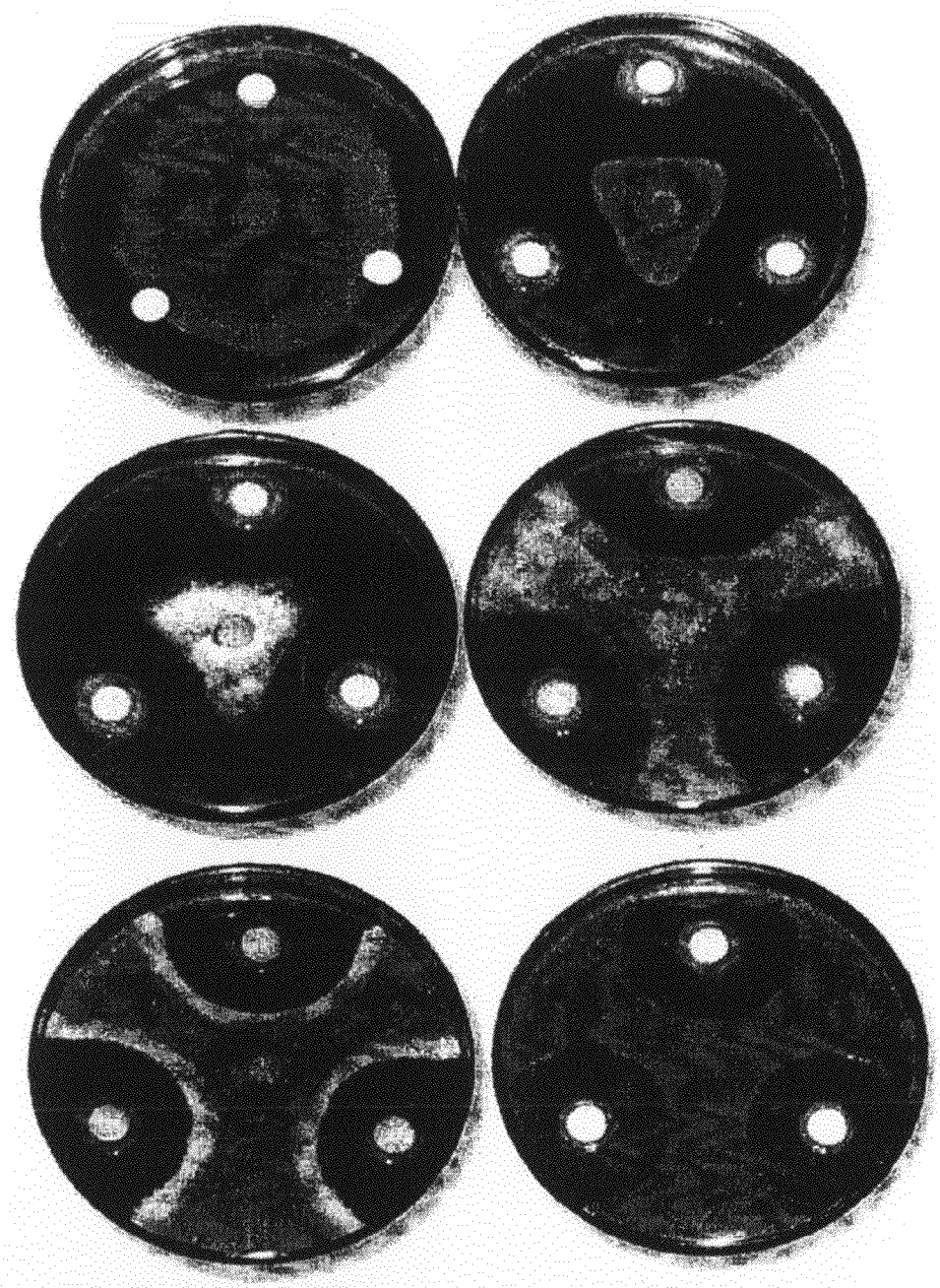
FIG. 2 shows the antibacterial and antifungal activities of the microorganisms according to the present invention.

In the present invention, microorganisms having the efficiency for removing the offensive odor of organic waste were first isolated in the following manner. Toxic substances were extracted from toxic plants, including *Aconiti ciliare, Aconitum carmichaeli, Quisqualis indica, Aconitum koreanum, Melia azedarah* var *japonica, Styrax japonica*, etc. and spread on soil to induce the mutation of microorganisms present in the soil. The soil was applied to organic waste and, as a result, it was observed that the soil had odor removal efficiency. Then, 24 kinds of microorganisms were isolated from the soil.

Among the above-isolated microorganisms, six kinds of microorganisms (SIP6728AF1, SJP6729AF2, SJP6730AF3, SJP6722A5, SJP6731B1 and SJP6735B6) having the effects of removing the offensive odor of organic waste, killing fiungi and insects and preventing decomposition were identified, and deposited in the Korean Culture Center of Microorganisms (KCCM), 361-221, Yurim BID, Hongje-1-dong, Seodaemun-gu, Seoul, Republic of Korea,which is an international depository authority under the Budapest Treaty. Also, among 24 kinds of microorganisms as described above, 11 kinds of microorganisms, which were free of nutrients and survived in a low-temperature environment, were measured for the effects of removing the offensive odor of organic waste, killing fungi and insects and preventing decompbsition; and 11 kinds of microorganisms (SJP6840AF4, SJP6844AF5, SJP6726AF6, SJP6843AF7, SJP6732B2, SJP6719B3, SJP6734B4, SJP6841L2, SJP6720L3, SJP6723L4 and SJP6742L5) showing the effects were identified, and deposited in KCCM. Among said 17 kinds of microorganisms deposited as described above, 7 kinds were identified as yeasts, and 10 kinds were identified as the genus *Bacillus*.

Said 17 kinds of SJP microorganisms were excellent with respect to the ability to ferment organic materials, decomposition-preventing ability, odor-preventing ability and insecticidav/fungicidal abilities. Particularly, the microbial strains (SJP6728AF1, SJP6729AF-2, SJP6730AF3, SJP6840AF4, SJP6726AF6, SJP6843AF7 and SJP6723L4) identified as yeasts were easily cultured in both anaerobic and aerobic environments and showed excellent abilities, except for fungicidal ability, compared to the abilities of the microbial strains (SJP6722A5, SJP6731B1, SJP6735B6, SJP6844AF5, SJP6732B2, SJP6719B3, SJP6734B4, SJP68411L2, SJP6720L3 and SJP6742L5) identified as the genus *Bacillus*. Said effects varied depending on the compositions of culture media.

Also, the effects of the genus *Bacillus* among the SJP microorganisms according to the present invention were analyzed and, as a result, the genus *Bacillus* found to have weak fermentation ability and insecticidal ability compared to the yeasts, but showed high antimicrobial effects in the order of SJP6735B6, SJP6841L2, SJP6722A5, SJP6732B2, SJP6719B3 and SJP6734B4 in antimicrobial tests.

When said microorganisms were continuously used in a specific system for 3 months or longer, the odor-preventing and harmful insect-controlling effects thereof were slowly decreased, but when said microorganisms were used in other systems placed in other locations, they again showed the effects shown in the previous system. This indicates that the odor-preventing and harmful insect-controlling activities of said microorganisms were relatively decreased due to microorganisms (putrefactive bacteria) having developed tolerance to specific microorganisms. Thus, when 1-2 kinds of microorganisms among said microorganisms are individually cultured, mixed with each other at a specific ratio and used while replacing them with other microorganisms at one-month intervals, a reduction in effects, caused by the tolerance of harmful bacteria, can be prevented.

Also, when said microorganisms were added to feed, digestion was promoted, and when these microorganisms were used in the preparation of fermented foods, fermented foods having better efficiency than that of prior fermentation methods could be prepared.

Among 7 kinds of SJP yeasts according to the present invention, SJP6728AF1 and SJP6729AF2, belonging to the genus *Saccharomyces*, can be used in fermented foods. This is because yeasts, the use of which is accepted as being in compliance with the Korean food additive code provided by the Korean Food and Drug Administration, are limited to the genus *Saccharomyces*, although said 7 kinds of yeasts has the same fermentation ability. The characteristics of the novel strains, SJP6728AF1 and SJP6729AF2, were compared with those of prior *S. exiguus* and, as a result, when *S. exiguus* was inoculated into food waste, an alcoholic odor was not generated even after 24 hours, but when food waste was treated with SJP6728AF1 and SJP6729AF2, an alcoholic odor could be sensed after 90 minutes.

EXAMPLES

Hereinafter, the present invention will be described in further detail with reference to specific examples. However, those skilled in the art will appreciate that these examples are not intended to limit the scope of the present invention, and various changes and modifications are possible within the sprit and scope of the present invention.

Example 1

Isolation and Identification of Novel Microorganisms and Insecticidal Microbicidal and Odor-Preventing Effects Thereof 1-1 Isolation of Microorganisms In order to screen microorganisms having strong tolerance to toxicity and strong survival ability and induce the mutation thereof, 300 g of toxic plants, including *Aconiti ciliare*, *Aconitum carmichaeli*, *Quisquals indica*, *Aconitum koreanum*, *Melia azedarah* var. *japonica*, and *Styrax japonica*, were diluted at the same amount, added to 3 liters of water, and subjected to hot-water extraction at 70~80° C. for 2-3 hours, thus extracting a toxic substance.

Said extract and salt were periodically spread onto various soils, including barren soil, rich soil, leaf mold and vermicompost, for about 6 months, and then the soils treated with the extract were collected, and applied to food waste compost fermentation facility located at Shiheung-shi, Kyunggi-do, Korea. As a result, 12 kinds of offensive odors, including ammonia and sulfide hydrogen, were measured to be 0.00 ppm (Table 1).

Moreover, when the extract-treated soils were applied to a container for separating and storing unrecyclable materials (vinyl bags, pig heads, fish, etc.) in the food waste compost fermentation facility, fly larvae were not generated.

In order to confirm microorganisms causing said effects, composts fermented with said extract-treated soils for 10 days and composts fermented with the soils for 30 days were collected, and analyzed at the Korean National Institute of Agricultural Science and Technology. As a result, 24 kinds of microorganisms, which were not present in prior composts untreated with the extract-treated soils, were detected and each of the microorganisms was isolated.

1-2: Insecticidal Effect Against Fly Larvae, Food Waste-Fermentation Effect and Odor-Preventing Effect Among said 24 kinds of microorganisms, 10 kinds of microorganisms were first randomly selected, and the insecticidal effect thereof against fly larvae and the odor-preventing effect thereof were then measured.

In the same manner as conventional methods of culturing yeasts, lactic acid bacteria or the genus *Bacillus* microorganisms, animals and plants containing nutrients, such as carbon sources, nitrogen sources, vitamins and minerals, were steamed at 121° C. and extracted to prepare a culture medium, and each of said 10 kinds of microorganisms was inoculated into the resulting culture medium and cultured at 30-45° C. for 24-62 hours. Solid microbial agents were prepared by inoculating each of said 10 kinds of microorganisms into organic solids, such as sterilized sawdust, rice bran, wheat bran, rice powder and corn powder and fermenting the inoculated organic solids.

In order to measure the insecticidal effect of said microorganisms against fly larvae, 5 liters of rotten fish, chicken and pork were left to stand at room temperature for 4 days to generate fly larvae. Then, the fly larvae were placed in each of the containers at a density of a minimum of about 500-1,000 larvae, and 10 ml of each of the 10 kinds of microorganism culture broth was added to 100 ml of water and applied to each of the containers. Then, the time and state, at which the fly larvae were killed, were examined. As a result, when the food wastes were treated with SJP6728AF1, SJP6722AF2, SJP6730AF3, SJP6722A5 and SJP6735B6, the fly larvae were killed (Table 2 and FIG. 1).

TABLE 1

Odors in food waste treatment plant

| Test item | Standard (ppm) | Result (ppm) |
|---|---|---|
| Ammonia | ≦2 | 0.0 |
| Methylmercaptane | ≦0.004 | 0.000 |
| Hydrogen sulfide | ≦0.06 | 0.00 |
| Dimethylsulfide | ≦0.05 | 0.00 |
| Dimethyldisulfide | ≦0.03 | 0.000 |
| Trimethylamine | ≦0.02 | 0.000 |
| Acetaldehyde | ≦0.1 | 0.00 |
| Styrene | ≦0.8 | 0.03 |
| Propionaldehyde | ≦0.1 | 0.00 |
| Butyraldehyde | ≦0.1 | 0.000 |
| n-Valeraldehyde | ≦0.02 | 0.000 |
| i-Valeraldehyde | ≦0.006 | 0.000 |
| Bad smell | ≦20 | 8 times |

Also, in the food waste compost fermentation facility, composts were produced in an amount of 12-13 tons/day and the water content thereof was 65-70%, but when the soils treated with the extract were applied to the plant, the production of composts was decreased to 5-6 tons/day, the water content thereof was 45-48%, and the volume thereof was also reduced to ⅓.

TABLE 2

Insecticidal effect against fly larvae

| Micro-organisms | Insecticidal rate (%) | Time (h) | Degrees of bad smell and the state of fly larvae |
|---|---|---|---|
| SJP6728AF1 | 100 | 4 | 3 days after death, fly larvae were decomposed to become clean water. After 5 days, the state of fish was changed weakly and it had a weak odor. |
| SJP6722AF2 | 100 | 2 | 3 days after death, carcasses of fly larvae were decomposed. After 5 days, the state of fish was changed weakly and bad odor disappeared. |
| SJP6730AF3 | 70 | 4 | After 12 hours, fish were half decomposed and were odorless. After 24 hours, fish were decomposed and 50% of fly larvae were active. |
| SJP6722A5 | 50 | 4 | After 12 hours, fish were decomposed and odorless. After 2 days, fly larvae were regenerated and they were vigorously active. |
| SJP6735B6 | 100 | 4 | After 12 hours, fish were decomposed to become a jelly-like state, odorless. After 5 days, half the fish remained and it had a weak odor. |

In order to measure an effect of said microorganisms on the fermentation of food waste, 20 ml of each of the 10 kinds of microorganism culture broth was spread onto 20 liters of food waste having a water content of about 65%, followed by agitation. Then, the food waste was warmed to maintain a temperature of 40-50° C. From 3 days after the microbial treatment, the degree of odor generation was measured using a sensory test and an odor meter.

As a result, when the food waste was treated with the SJP6728AF1, SJP6722AF2, SJP6730AF3, SJP6722A5, SJP6731B1 and SJP6735B6 microbial strains, the freshness thereof was not changed and it was odorless (Table 3). This indicates that SJP6728AF1, SJP6722AF2, SJP6730AF3, SJP6722A5, SJP6731B1 and SJP6735B6 have an excellent ability to prevent decomposition.

TABLE 3

Results of food waste fermentation

| Microorganisms | Deodorization effect (%) | Period (day) | Sensory test result |
|---|---|---|---|
| SJP6728AF1 | 100 | 3 | odorless |
| SJP6722AF2 | 100 | 3 | odorless |
| SJP6730AF3 | 100 | 3 | odorless |
| SJP6722A5 | 100 | 3 | odorless |
| SJP6731B1 | 100 | 3 | odorless |
| SJP6735B6 | 100 | 3 | odorless |

Also, in order to measure the odor-preventing effect of said microorganisms, 5 ml of each of said 10 kinds of microorganism culture broth was applied to wastewater (BOD 100,000 ppm) generated in food waste, and a change in the offensive odor of the wastewater was measured using an odor meter.

As a result, when the wastewater was treated with SJP6728AF1, SJP6722AF2 and SJP6730AF3, more than 90% of the offensive odor thereof was removed 90 minutes after the microbial treatment, and the offensive odor thereof was not generated even 6 days after the microbial treatment (Table 4).

TABLE 4

Odor of food wastewater

| Microorganisms | Deodorization effect (%) | Time (min) | Effect | Alcohol conc. (%) |
|---|---|---|---|---|
| SJP6728AF1 | 90 | 90 | After 90 min, bad odor disappeared and alcohol smell was generated | 8 |
| SJP6722AF2 | 90 | 90 | After 90 min, bad odor disappeared and alcohol smell was generated | 7.5 |
| SJP6730AF3 | 90 | 90 | After 90 min, bad odor disappeared and alcohol smell was generated | 7.5 |

Before and after collecting food waste into food waste collection containers, 20-50 ml of each of said 6 kinds of microorganism culture broth (SJP6728AF1, SJP6722AF2, SJP6730AF3, SJP6722A5, SJP6731B11 and SJP6735B6) was spread into the food waste, the offensive odor of the wastewater was not generated not only in the collection containers, but also in collection vehicles and pretreatment systems, and the offensive odor thereof and fly larvae were not generated even when the food waste was not collected for 3-5 days (a maximum of 10 days).

1-3: Measurement of Antibacterial and Antifungal Activities

The antibacterial and antifungal activities of said 6 kinds of microorganisms (SJP6728AF1, SJP6722AF2, SJP6730AF3, SJP6722A5, SJP6731B1 and SJP6735B6) against plant pathogenic bacteria were measured at the Plant Pathological Department, the Biological Division, the Korean National Institute of Agricultural Science and Technology. Bacteria and fungi were inoculated into SDA (Sabouraud dextrose agarblock) and cultured for 48 hours. Then, a block immersed in each of said 6 kinds of microbial culture broth for 5 minutes was inoculated into the media having the bacteria and fungi cultured therein, and were cultured at 15° C. in a dark condition for 24 hours, and the diameter of colonies formed by the bacteria was measured in units of mm. As a result, the antibacterial and antifungal activities of SJP6728AF1, SJP6722AF2, SJP6730AF3, SJP6722A5, SJP6731B1 and SJP6735B6 microorganisms were shown to be high (Table 5 and FIG. 2).

TABLE 5

Antibacterial and antifungal activities of SJP microorganisms

| | Activities | | | | | |
|---|---|---|---|---|---|---|
| | AF1 | AF2 | AF3 | A5 | B1 | B6 |
| Bacteria | | | | | | |
| Agrobacterium vitis | − | − | − | + | − | ++ |
| Clavibacter michiganensis subsp. michiganensis | + | − | − | + | − | ++ |
| Pectobacterium carotovorum subsp. carotovorum | − | − | − | + | − | + |
| Xanthomonas campestris pv. campestris | − | − | − | + | − | + |
| Fungi | | | | | | |
| Colletotrichum gloeosporides | − | + | − | + | + | +++ |
| Fusarium oxysporum | − | − | − | + | + | +++ |
| Phytophthora capsici | − | − | − | − | − | + |
| Rhizoctonia solani | + | + | + | + | − | ++ |
| Sclerotinia sclerotiorum | + | + | + | + | − | ++ |

Activity grade:
− non-activity
+ weak
++ moderate
+++ excellent 1-4: Identification of Microorganisms SJP6728AF1, SJP6729AF2, SJP6730AF3, SJP6722A5, SJP6731B1 and SJP6735B6 were identified at the Korean Culture Center of Microorganisms (KCCM) and, as a result, the 18S rDNAs of SJP6728AF1 (SEQ ID NO: 1) and SJP6729AF2 (SEQ ID NO: 2) showed a homology of 97% to *Saccharomyces exiguus*, the 18S rDNA of SJP6730AF3 (SEQ ID NO: 3) showed a homology of 97% to *Candida fructus*. Also, the 16S rDNA of SJP6722A5 (SEQ ID NO: 4) showed a homology of 98% to *Lactobacillu paraplantarum*, the 16S rDNA of, SJP6731B1 (SEQ ID NO: 5) showed a homology of 99% to *Bacillus badius*, and the 16S rDNA of SJP6735B6 (SEQ ID NO: 6) showed a homology of 99% to *Paenibacillus polymyxa*. Each of said microbial strains was deposited in the Korean Culture Center of Microorganisms (KCCM) (Table 6).

TABLE 6

Name and deposit number of SJP microorganisms

| Name | Deposit number |
|---|---|
| SJP6728AF1 | Saccharomyces exiguus KCCM-10675P* |
| SJP6729AF2 | Saccharomyces exiguus KCCM-10677P* |
| SJP6730AF3 | Candida fructus KCCM-10679P |
| SJP66722A5 | Lactobacillu paraplantarum KCCM-10676P |
| SJP6731B1 | Bacillus badius KCCM-10680P |
| SJP6735B6 | Paenibacillus polymyxa KCCM-10678P |

*Deposited 26 Aug. 2005

Example 2

Secondary Isolation and Identification of Microorganisms and Insecticidal, Microbicidal and Odor-Preventing Effects Thereof 2-1: Secondary Isolation of Microorganisms 24 kinds of culture broth isolated in Example 1 were stored in a refrigerator at 3° C. for 90 days, and survived microbial strains were examined. As a result, 8 kinds of microorganisms (SJP6840AF4, SJP6844AF5, SJP6726AF4, SJP6843AF7, SJP6841L2, SJP6719B3, SJP6734B4 and SJP6723L4) survived. Said 14 kinds of previously untested strains and said 8 kinds of secondarily isolated strains were measured with respect to an insecticidal effect against fly larvae, effects on organic waste fermentation and odor prevention, and antibacterial and antifungal effects.

2-2: Measurement of Insecticidal Effect Against Fly Larvae and Effects on Food Waste Fermentation and Odor Prevention 5 liters of each of rotten fish, chicken and pork was placed in containers and left to stand at room temperature for 4 days to generate fly larvae. The fly larvae were placed in each of the containers at a density of a minimum of about 500-1,000 larvae, and 10 ml of each of said 22 kinds of microorganism culture broth (14 kinds of previously untested microbial strains and 8 kinds of secondarily isolated strains) was added to 100 ml of water and applied to the fly larva-containing containers. Then, the time and state, at which the fly larvae were killed, were examined.

As a result, when the food wastes were treated with each of 11 kinds of microorganisms (SJP6840AF4, SJP6844AF5, SJP6726AF6, SJP6843AF7, SJP6732B2, SJP6719B3, SJP6734B4, SJP6841L2, SJP6720L3, SJP6723L4 and SJP6742L5), 50-100% of the fly larvae were killed 2-6 hours after the microbial treatment. After 2 days, in the case of treatment with each of SJP6732B2, SJP6719B3 and SJP6841L, fly larvae began to be generated again, and odors were also generated after 3 days. However, in the case of treatment with each of SJP6840AF4, SJP6844AF5, SJP6726AF6, SJP6843AF7, SJP6734B4 and SJP6841L2, the freshness of the fish and chicken was not changed even 3 days after the microbial treatment, and more than 70% of the freshness was changed 6 days after the microbial treatment, but the offensive odor of the food wastes was not generated (Table 7).

TABLE 7

Insecticidal effect against fly larvae

| Microorganisms | Insecticidal rate (%) | Time of death (day) |
|---|---|---|
| SJP6840AF4, SJP6844AF5, SJP6734B4, SJP6841L2 | 100 | 2 |
| SJP6726AF6, SJP6843AF7 | 100 | 3 |
| SJP6720L3, SJP6723L4, SJP6742L5 | 60~70 | 6 |
| SJP6732B2, SJP6719B3 | 40~50 | 6 |

Also, 20 ml of each of said 22 kinds of microorganism culture broth (14 kinds of previously untested strains and 8 kinds of secondarily isolated strains) was applied to 10 liters of food waste having a water content of about 65%. Then, the food waste was agitated and then warmed to maintain a temperature of 40-50° C. From 3 days after the microbial treatment, the degree of odor generation was continuously measured using a sensory test and an odor meter.

As a result, said 11 kinds of microorganisms (SJP6840AF4, SJP6844AF5, SJP6726AF6, SJP6843AF7, SJP6732B2, SJP6719B3, SJP6734B4, SJP6841L2, SJP6720L3, SJP6723L4 and SJP6742L5), which showed an excellent insecticidal effect against fly larvae, also showed an excellent fermentation effect (Table 8).

TABLE 8

Effects on food waste fermentation

| Microorganisms | Fermentation effect (%) | Fermentation period (day) |
|---|---|---|
| SJP6840AF4, SJP6844AF5, SJP6726AF6, SJP6843AF7 | 100 | 3 |
| SJP6732B2, SJP6719B3, SJP6734B4, SJP6841L2, SJP6720L3, SJP6723L4, SJP6742L5 | 80 | 3 |

Said 11 kinds of microorganisms (SJP6840AF4, SJP6844AF5, SJP6726AF6, SJP6843AF7, SJP6732B2, SJP6719B3, SJP6734B4, SJP6841L2, SJP6720L3, SJP6723L4 and SJP6742L5) were measured with respect to the effect of preventing the offensive odor of wastewater generated in food waste. 5 ml of each of said 11 kinds of microbial culture broth was applied to 10 liters of food wastewater (BOD 100,000 ppm), and a change in the offensive odor of the wastewater was measured using an odor meter (FIG. 3).

As a result, in the group treated with each of 10, SJP6840AF4, SJP6844AF5, SJP6726AF6 and SJP6843AF7 strains, the offensive odor thereof disappeared 1 hour after the microbial treatment, and an alcoholic odor began to be generated at 90 minutes after the microbial treatment. The liquids of the treated groups having the alcoholic odor were distilled to measure the specific gravity thereof, and the measurement results showed that the group treated with each of SJP6840AF4, SJP6844AF5, SJP6726AF6 and SJP6843AF7 had an alcohol concentration of 6-8% (Table 9).

TABLE 9

Alcohol concentration of food waste

| Microorganisms | Time (min) | Alcohol conc. (%) |
|---|---|---|
| SJP6840AF4, SJP6844AF5, SJP6726AF6, SJP6843AF7 | 90 | 6~8 |
| SJP6732B2, SJP6719B3, SJP6734B4, SJP6841L2, SJP6720L3, SJP6723L4 | 90 | 3~5 |

Also, the acidity of the food waste was measured, and the measurement results showed that the group treated with each of the SJP6840AF4, SJP6844AF5, SJP6726AF6 and SJP6843AF7 strains had pH 3.7, the group treated with each of SJP6732B2 and SJP6719B3 had pH 4.2, and the group treated with each of SJP6841L2 and SJP6720L3 had pH 4.1. Also, the group treated with each of said 11 kinds of microorganisms did not generate odors, even when they were left to stand in a compost fermentation system at 35-40° C. for more than 1 month.

2-3: Antibacterial and Antifungal Activities

In order to examine whether said 11 kinds of microorganisms (SJP6840AF4, SJP6844AF5, SJP6726AF6, SJP6843AF7, SJP6732B2, SJP6719B3, SJP6734B4, SJP6841L2, SJP6720L3, SJP6723L4 and SJP6742L5) show antibacterial activity against bacteria and fungi that damage the crops, the antibacterial and antifungal activities of said microorganisms were measured at the Plant Pathological Department, the Biological Division, the Korean National Institute of Agricultural Science and Technology, using bacteria and fungi conserved in the Korean National Institute of Agricultural Science and Technology.

Bacteria and fungi were inoculated into SDA (Sabouraud dextrose agarblock) and cultured for 48 hours. Then, a block immersed in each of said 11 kinds of microbial culture broth for 5 minutes was inoculated into the medium having the bacteria and fungi cultured therein, and then cultured in a dark condition at 15° C. for 24 hours. The diameter of colonies formed by the bacteria was measured in units of mm (Table 10).

Also, 30 liters of food waste was left to stand in a compost fermentation chamber for 7 days so as to be completely decomposed, and the density of putrefactive bacteria causing ammonia, hydrogen sulfide and the like was analyzed using a streak plate method. As a result, the putrefactive bacteria were detected at a density of $3-15\times10^8$ bacteria/ml. The putrefactive bacteria were inoculated with 10 ml of each of SJP6840AF4, SJP6719B3 and SJP6841L2 culture broth and cultured for 2 hours, and the density of putrefactive bacteria in each of the culture broth was examined using a dilution plate method. As a result, the group treated with SJP6840AF4 had putrefactive bacteria detected at a density of about $2-5\times10^2$/ml, the group treated with SJP6719B3 had putrefactive bacteria detected at a density of about $2-5\times10^3$/ml, and the group treated with SJP6841 L2 had putrefactive bacteria detected at a density of about $2-5\times10^3$/ml. This suggests that SJP6840AF4, SJP6719B3 and SJP6841L2 have antibacterial activity.

TABLE 10

Antibacterial and antifungal activities of SJP microorganisms

| | Name | Abbreviation |
|---|---|---|
| Bacteria | *Agtobacterium vifis* | Ag |
| | *Clavibacter michiganensts* subsp. *michiganensis* | Cl |
| | *Erwinia carotovora* subsp. *carotovora* | Er |
| | *Xanthomonas campestris* pv. *campestris* | Xa |
| Fungus | *Colletotrichum gloeosporioides* | Co |
| | *Fusarium oxysporum* | Fu |
| | *Phytophthora capsici* | Ph |
| | *Rhizoctonia solani* | Rh |
| | *Sclerotinia sclerotiorum* | Sc |

Anti-microbial activity of SJP microorganisms

| Microorganisms | Ag | Cl | Er | Xa | Co | Fu | Ph | Rh | Sc |
|---|---|---|---|---|---|---|---|---|---|
| SJP6840AF4 | | + | − | − | − | − | − | + | − |
| SJP6844AF5 | + | − | − | − | − | + | − | + |
| SJP6726AF6 | − | − | − | − | − | − | + | − | + |
| SJP6843AF7 | − | − | − | + | − | − | − | − | − |
| SJP6732B2 | + | + | + | + | + | + | − | + | + |
| SJP6719B3 | + | + | ++ | + | + | +++ | ++ | + | − |
| SJP6734B4 | ++ | − | + | ++ | − | ++ | +++ | + | ++ |
| SJP6841L2 | ++ | ++ | ++ | + | +++ | +++ | +++ | ++ | ++ |
| SJP6720L3 | + | + | + | ++ | + | ++ | + | + | ++ |
| SJP6723L4 | + | − | − | + | ++ | + | − | − | + |
| SJP6742L5 | + | + | + | + | ++ | + | + | ++ | + |

Activity grade:
− non-activity
+ weak
++ moderate
+++ excellent 2-4: Identification of Microorganisms Said 11 kinds of microorganisms (SJP6840AF4, SJP6844AF5, SJP6726AF6, SJP6843AF7, SJP6732B2, SJP6719B3, SJP6734B4, SJP6841L2, SJP6720L3, SJP6723L4 and SJP6742L5) were identified at the Korean Culture Center of Microorganisms and, as a result, the 16S rDNAs of SJP6840AF4 (SEQ ID NO: 7) and SJP6843AF7 (SEQ ID NO: 8) showed a homology of 99% to *Candida zeylanoides*, the 16S rDNA of SJP6844AF5 (SEQ ID NO: 9) showed a homology of 99% to *Kazachstania aerobia*, and the 16S rDNA of SJP6726AF6 (SEQ ID NO: 10) showed a homology of 99% to *Candida humilis*. Also, the 16S rDNA of SJP6732B2 (SEQ ID NO: 11) showed a homology of 99% to *Paenibacillus lactis*, the 16S rDNA of SJP6719B3 (SEQ ID NO: 12) showed a homology of 99% to *Paenibacillus* sp. AY397772, and the 16S rDNA of SJP6734B4 (SEQ ID NO: 13) showed a homology of 99% to *Brevibacillus borstelensis*. In addition, the 16S rDNA of SJP6841L2 (SEQ ID NO: 14) showed a homology of 99% to *Lactobacillus casei*, the 16S rDNA of SJP6720L3 (SEQ ID NO: 15) showed a homology of 99% to *Lactobacillus brevis*, the 16S rDNA of SJP6723L4 (SEQ ID NO: 16) showed a homology of 99% to *Leuconostoc citreum*, and the 16S rDNA of SJP6742L5 (SEQ ID NO: 17) showed a homology of 99% to *Camobacterium maltaromaticum*. Each of these microbial strains was deposited in the Korean Culture Center of Microorganisms (KCCM) (Table 11).

TABLE 11

Name and deposit number of SJP microorganisms

| Name | Deposit number |
|---|---|
| SJP6840AF4 | *Candida zeylanoides* KCCM-10695P |
| SJP6844AF5 | *Kazachstania aerobia* KCCM-10696P |
| SJP6726AF6 | *Candida humilis* KCCM-10697P |
| SJP6843AF7 | *Candida zeylanoides* KCCM-10698P |
| SJP6732B2 | *Paenibacillus lactis* KCCM-10726P |
| SJP6719B3 | *Paenibacillus* sp. AY397772 KCCM-10727P |
| SJP6734B4 | *Brevibacillus borstelensis* KCCM-10728P |
| SJP6841L2 | *Lactobacillus casei* KCCM-10729P |
| SJP6720L3 | *Lactobacillus brevis* KCCM-10730P |
| SJP6723L4 | *Leuconostoc citreum* KCCM-10731P |
| SJP6742L5 | *Camobacterium maltaromaticum* KCCM-10732P |

Comparative Example 1

Fly Larva-Killing Effect and Food Waste Fermentation Effect of Similar Microbial Strains Microbial strains most similar to the inventive microorganisms were purchased or distributed from the Korean Agricultural Culture Collection (KACC), the Korean Culture Collection of Microorganisms (KCCM), and the Korean Collection for Type Cultures (KCTC). Whether the distributed microbial strains have an insecticidal effect against fly larvae, an odor-preventing effect and an organic waste-fermentation effect was examined according to the above-described methods (Table 12 and Table 13).

TABLE 12

Insecticidal effect against fly larvae

| Similar microorganisms | Insecticidal rate (%) | Time of death (h) |
|---|---|---|
| Candida zeylanoides, Candida humilis | 0 | 12 |
| Lactobacillus casei, Lactobacillus brevis, Camobacterium maltaromaticum, Brevibacillus borsterensis | 10~20 | 9 |
| Paenibacillus sp., Paenibacillus lactis, Lactobacillus ctreum | 20~30 | 6 |

TABLE 13

Fermentation effect of food waste

| Similar microorganisms | Fermentation effect (%) | Fermentation period (day) |
|---|---|---|
| Candida zeylanoides, Candida humilis, Kazachstania aerobia | 50 | 3 |
| Camobacterium maltaromaticum, Brevibacillus borsterensis | 30 | 3 |
| Lactobacillus casei, Lactobacillus brevis, Paenibacillus sp., Paenibacillus lactis, Lactobacillus ctreum | 10 | 3 |

The results of examination of the insecticidal effect against fly larvae showed that the case of treatment with *Paenibacillus* sp. showed a death rate of 30%, but vigorous fly larvae regeneration occurred again only, 10 hours after the microbial treatment. Also, the odor-preventing effects of the distributed microorganisms were significantly lower than those of the case treated with each of 17 kinds of microbial strains (SJP6728AF1, SJP6729AF2, SJP6730AF3, SJP6722A5, SJP6731B1, SJP67315B6, SJP6840AF4, SJP6844AF5, SJP6726AF6, SJP6843AF7, SJP6732B2, SJP6719B3, SJP6734B4, SJP6841L2, SJP6720L3, SJP6723L4 and SJP6742L5) according to the present invention.

Example 3

Insecticidal Effect Against Mosquito Larvae

In order to examine the insecticidal effect of the microorganisms identified in Example 2 against mosquito larvae, 10 ml of each of said 11 kinds of microbial culture broth (SJP6840AF4, SJP6844AF5, SJP6726AF6, SJP6843AF7, SJP6732B2, SJP6719B3, SJP6734B4, SJP6841L2, SJP6720L3, SJP6723L4 and SJP6742L5) was applied to mosquito larvae. In the group treated with each of SJP6734B4 and SJP6841L2, the mosquito larvae began to be killed 6 hours after the microbial treatment, and were all killed 9 hours after the microbial treatment. In the group treated with SJP6732B2, the mosquito larvae began to be killed 8 hours after the microbial treatment and were all killed 12 hours after the microbial treatment.

Example 4

Analysis of Composts Fermented with SJP Microorganisms

Composts fermented using 17 kinds of microorganisms according to the present invention for 10 days and 30 days were not thermally treated. On the other hand, composts fermented in these conditions were thermally treated at 70° C. for 10 minutes. Then, the density of each of the microorganisms in the composts was measured using a streak plate method (Table 14).

As a result, in the fermented composts treated with the inventive microorganisms, microorganisms were detected in an amount about 12-56 times larger than those in the control group, and the density of fungi was relatively low. However, in the composts-fermented using the inventive microorganisms for 10 days, the density of yeasts was high compared to the control group.

TABLE 14

Density of microorganisms in compost samples (unit: $\times 10^6$ CFU/g)

| | Bacteria | | | |
|---|---|---|---|---|
| Samples | Non-heat treatment | Heat treatment (70° C., 10 min) | Fungi | Yeasts |
| The inventive microorganism treated compost (10 day fermentation) | 56.0 | 1.0 | 0.07 | 0.32 |
| The inventive microorganism treated compost (30 day fermentation) | 12.3 | 2.4 | 0 | 0 |
| General compost | 1.1 | 0.1 | 0.73 | 0 |

Also, it was found that microorganisms detected in the composts treated with the inventive microorganisms consisted mainly of the genus *Bacillus* and yeasts, microorganisms having an odor reduction effect and an insecticidal effect against fly larvae were detected in the composts treated with the inventive microorganisms, and microorganisms having an antibacterial activity against plant pathogenic bacteria, and microorganisms promoting the growth of plants, were detected in the composts treated with the inventive microorganisms. This indicates that the microorganisms having an effect on odor reduction can be used in food waste and livestock manure, and the microorganisms having an antibacterial activity, a plant growth-promoting effect and an insecticidal effect against fly larvae can be used as agents for controlling disease and insect pests.

The primarily isolated and identified SJP6728AF1, SJP6729AF2 and SJP6730AF3, and the secondarily isolated and identified SJP6840AF4, SJP6844AF5, SJP6726AF6, SJP6732B2, SJP6719B3, SJP6743B4, SJP6841L2 and SJP6720L3, were cultured in one medium at 35° C. for 3 days, and the organic waste fermentation effect thereof and the insecticidal effect thereof against fly larvae were measured. As a result, it was found that the use of a mixture of two or more of the inventive microbial strains provided excellent effects compared to when the microbial strains were used alone.

Also, the microorganisms according to the present invention showed effects varying depending on medium compositions. In other words, when 17 kinds of microorganisms according to the present invention were inoculated and cultured in a medium made of only rice bran, and the insecticidal effect thereof against fly 5, larvae was then measured, SJP6728AF1, SJP6726AF6 and SJP6719B3 were most effective. However, in a medium made of only wheat bran, SJP6844AF5, SJP6743B4 and SJP6841L2 showed the most excellent effects.

Example 5

Odor-Preventing Effect

The odor-preventing effects of 17 kinds of microorganisms (SJP6728AF1, SJP6729AF2, SJP6730AF3, SJP6722A5, SJP6731B1, SJP6735B6, SJP6840AF4, SJP6844AF5, SJP6726AF6, SJP6843AF7, SJP6732B2, SJP6719B3, SJP6734B4, SJP6841L2, SJP6720L3, SJP6723L4 and SJP6742L5) according to the present invention were analyzed at the Department of Earth & Environmental Sciences, Sejong, University. After making fish and meats rotten, said 17 kinds of microorganisms were inoculated into the rotten fish and meats. Then, a change in the offensive odor of the fish and meats was measured using an odor meter for 30 days after the microbial treatment.

As a result, the offensive odor of the fish and meats was several thousand-fold reduced 1 hr~1 day after the microbial treatment. The offensive odor was reduced with the passage of time and reduced to $\frac{1}{7}$ after 7 days. Particularly, hydrogen sulfide decreased by 99.99% so that there was no trace of the offensive odor, and the offensive odor was generated again after 30 days. However, it could be seen that the inventive microorganisms are effective in preventing odors, considering that most organic wastes are disposed of within 2-3 days. Also, because the inventive microorganisms show an odor-preventing effect and a decomposition preventing effect for 30 days, they are useful as preservatives for maintaining the freshness of fish, vegetable and the like.

Example 6

Tests on Cattle, Pig and Chicken Feeds

Solid organic materials, such as rice bran, wheat bran and soybean, were mixed with water to a water content of 65-70%, and agitated such that water was uniformly absorbed into the organic materials. The agitated materials were sterilized with steam, and then inoculated with at least one microorganisms selected from among said microorganisms. The resulting materials were cultured for 30-40 hours, dried and milled, thus preparing feed additives.

In another method, one or more microorganisms selected from among said 17 kinds of microorganisms (SJP6728AF1, SJP6729AF2, SJP6730AF3, SJP6722A5, SJP6731B1, SJP6735B6, SJP6840AF4, SJP6844AF5, SJP6726AF6, SJP6843AF7, SJP6732B2, SJP6719B3, SJP6734B4, SJP6841L2, SJP6720L3, SJP6723L4 and SJP6742L5) according to the present invention were cultured in a liquid broth, and then mixed with solid organic materials such as rice bran, wheat bran and soybean, thus preparing livestock feed additives. In still another method, one or more microorganisms selected from among 17 kinds of microorganisms (SJP6728AF1, SJP6729AF2, SJP6730AF3, SJP6722A5, SJP6731B1, SJP6735B6, SJP6840AF4, SJP6844AF5, SJP6726AF6, SJP6843AF7, SJP6732B2, SJP6719B3, SJP6734B4, SJP6841L2, SJP6720L3, SJP6723L4 and SJP6742L5) according to the present invention were cultured in a liquid broth and dried, and then the dried microorganisms were mixed with solid organic materials, such as rice bran, wheat bran and soybean, thus preparing feed additives or feeds. As additives for water, three or more microorganisms selected from among the inventive microorganisms were mixed with each other at a specific ratio, and diluted in water at a concentration of 1-2%.

In the cattle manure of control group, which was not fed with the feed additives or water additives prepared as described above, corn used as cattle feed was evacuated from the bowels without digestion, but in the manure of cattle fed with the feed additives or water additives, corn used as feed was not seen (FIG. 4). This indicates that the SJP microorganisms according to the present invention have the effect of promoting digestion.

Also, plants such as maize and Scutellaria baicalensis, which are rich in yellow pigments (xanthophyll, carotene, etc.), tend to show a deeper yellow color when they are fermented. Thus, when the SJP microorganism culture broth according to the present invention were added to chicken feed, the skin of the resulting chicken, the shell of the eggs, and the yellow eggs, showed a deeper yellow color.

Example 7

Substitution for Growth-Promoting Antibiotics in Pig Feed

The verification of the antibiotic-substitution, growth-promoting effect, feed-saving effect and odor- and fly-preventing effects of the inventive microorganisms was conducted on pigs. 40% rice bran, 30% wheat bran and 30% mixture of red pepper seeds, Scutellana baicalensis, ginger, cinnamon and licorice were powdered, sterilized, and cultured with each of SJP6728AF1, SJP6720L3 and SJP6732B2, thus preparing feed additives. Pigs were fed with the feed additives to confirm whether the microorganisms can substitute for antibiotics. Finishing pigs (50.5 kg) were allotted to three treatment groups (four replications per treatment), and in order to reduce a deviation in body weight and an error caused by the division between male and female pigs, total test pigs were divided into four groups (two female groups and two castrated male groups) according to body weight and sex. In a control group, antibiotics (55 ppm neomycin+110 ppm terramycin) were added. Also, an antibiotic-free control group was used, and the culture broth of the inventive microorganisms was added to water at a concentration of 2.5%, and then the pigs were fed with water to confirm the effect of substituting for antibiotics (table 15).

TABLE 15

Substitution test of antibiotics with SJP microorganisms

| | Weight gain (g) | Feed intake (g) | Feed efficiency[a] | Remark |
|---|---|---|---|---|
| Antibiotic feed control | 840.9 | 1908.0 | 2.28 | 20 pigs (female and male) 4 repetition |
| Non-antibiotic feed control | 695.4 | 1830.0 | 2.61 | 20 pigs (female and male) 4 repetition |
| SJP microorganism treatment group without antibiotics | 818.8 | 1839.1 | 2.25 | 20 pigs (female and male) 4 repetition |

[a]"Feed efficiency" = Feed intake/Weight gain

As a result, the group fed with the feed additive inoculated with the inventive SJP microorganisms without treatment with antibiotics showed a daily body weight gain similar to that of the control group fed with the antibiotic-containing feed, and a feed efficiency of 2.25 similar to that of the control group fed with the antibiotic-containing feed. This suggests that the microorganisms according to the present invention are useful as antibiotic substitutes.

Also, the effects of the SJP microorganisms according to the present invention on the number of bacteria in manure and the generation of odor were analyzed. The manure of livestock was collected before it falls onto soil, and the total bacterial number, the number of *E. coli* and the number of lactic acid bacteria in the collected manure were measured using a streak plate method. The amount of noxious gases generated was measured by analyzing ammonia and hydrogen sulfide using an odor analyzer, and the data were subjected to the analysis of variance using ANOVA of the SAS package. The test of significance between the groups was performed using Duncan's new multiple range test (Steel and Torrie), the confidence level was 95% (Table 16).

As a result, in the case where 3 kinds of SJP microorganism culture broth were administered to pigs, there was no change in the total number of bacteria in the bowels of the pigs, but the number of *E. coli* as harmful bacteria was greatly reduced. Also, the results of analysis of noxious gases showed that, when the feed additive was treated with the inventive microorganisms, the generation of ammonia and hydrogen sulfide among noxious gases in the pig manure was decreased.

TABLE 16

Number of bacteria and amount of harmful gases generated in manure upon addition of SJP microorganisms

| Treatment | T1 (Antibiotic feed) | T2 (Non-antibiotic feed) | T3 (SJP addition without antibiotics) | LSD (0.05) |
|---|---|---|---|---|
| Number of bacteria | | | | |
| Total bacteria | $22.3 \times 10^6$ | $35.2 \times 10^6$ | $33.1 \times 10^6$ | NS |
| E. coli | $37.2 \times 10^4$ | $32.1 \times 10^4$ | $9.3 \times 10^4$ | 22.2 |
| Harmful gas (ppm) | | | | |
| Ammonia | 1.4 | 1.8 | 0.3 | 0.8 |
| Hydrogen sulfide | 49.0 | 31.5 | 0.1 | 22.0 |

Example 8

Substitution for Growth-Promoting Antibiotics in Chicken Feed

The effect of feed additives containing the inventive microorganisms (SJP6728AF1 SJP67225A5 and SJP6841L2) on the production of chicken was measured. 270 chickens were allotted to 3 treatment groups (3 replications per treatment), so that the animals were divided into a control group administered with a dilution of antibiotics (0.05% virginiamycin and 0.03% anticoccidium agent), and groups treated with 0.5% and 1.0% feed additives fermented using the SJP microorganism culture broth (SJP6728AF1, SJP67225A5 and SJP6841L2) according to the present invention. The animal groups were bred for 5 weeks to analyze the production of chicken (Table 17).

Also, mortality and growth ratio were analyzed according to the number of chickens killed during the chicken-raising period of 5 weeks (Table 18), the enteric microorganisms of the chickens were analyzed (Table 19), and the offensive odor of the chicken manure was measured using an odor meter (Table 20).

TABLE 17

Effect of SJP microorganism-containing feed additive on production of chicken.

| | Antibiotic feed control | 0.5% feed additive with SJP | 1.0% feed additive with SJP |
|---|---|---|---|
| Initial weight (g/number) | 46.1 | 46.8 | 46.7 |
| Final weight (g/number) | 1,507 | 1,537 | 1,582 |
| Weight gain (g/number) | 1,461 | 1,490 | 1,535 |
| Feed intake (g/number) | 2,344 | 2,300 | 2,376 |
| Feed demand ratio[a] | 1.61 | 1.55 | 1.55 |

[a]Feed demand ratio = Feed intake/Weight gain

TABLE 18

Mortality and growth ratio of chicken

| | Antibiotic feed control | 0.5% feed additive with SJP | 1.0% feed additive with SJP |
|---|---|---|---|
| Mortality (%) | 1.1 | 1.2 | 0 |
| Growth ratio (%) | 98.9 | 98.3 | 100 |

TABLE 19

Number of enteric microorganisms (5 weeks)

| | Antibiotic feed control | 0.5% feed additive with SJP | 1.0% feed additive with SJP |
|---|---|---|---|
| | $Log_{10}$ cfu/g | | |
| Total number | 8.122 | 7.797 | 7.924 |
| E. coli | 7.350 | 7.022 | 6.579 |
| Lactobacillus sp. | 8.322 | 8.463 | 8.717 |

TABLE 20

Odors of chicken manure

| | Antibiotic feed control | 0.5% feed additive with SJP | 1.0% feed additive with SJP |
|---|---|---|---|
| Ammonia (ppm) | 2.1 | 0.14 | 0.18 |
| Hydrogen sulfide (ppm) | 78.5 | 0.23 | 0.16 |

As a result, the groups treated with the inventive SJP microorganisms resulted in high production rate, low mortality, decreased feed amount, and decreased odors, compared to those of the group treated with the antibiotics. Also, the test pig meat and chicken meat were boiled in pure water and tasted by 50 persons. As a result, the 50 persons all evaluated that the inventive meat were soft, had reduced characteristic odor and good taste, compared to prior meats. Accordingly, treatment with the SJP microorganisms according to the present invention enables eco-friendly livestock products to be produced without using antibiotics.

Example 9

Feed Additives Fermented with Chinese Herbs

The SJP microorganisms according to the present invention survived upon application of natural insecticides made of toxic plants, and thus whether the inventive microorganisms can solve a problem of toxicity present in ginkgo leaves and Chinese herbs was examined. First, 200 g of ginkgo leaves were subjected to hot water extraction in 1.5 liters of water, and the extract was inoculated with each of said 17 kinds of SJP microorganism culture broth according to the present invention. The resulting extract was placed in a heating cabinet maintained at 40° C. together with a control group non-inoculated with the inventive microorganisms, and then fermented for 24 hours. Then, whether gas was generated in the treated group and the control group was analyzed. As a result, gas was not generated in the control group, whereas gas was generated in the group treated with the inventive SJP microorganisms.

In all the extracts treated with said 17 kinds of microorganisms, gas was not generated for 7 days, and thus the fermentation of the extracts was considered to be terminated. In order to examine whether the inventive microorganisms counteracted the poisonous effects, a toxicity test on the extracts was performed by a sensory test by sensing the extracts with the tongue in the mouth. As a result, the extracts fermented with the inventive SJP microorganisms gave soft sensation without rejection. However, the non-fermented extract resulted in gnawing sensation, vomiting symptoms, a biting taste, and offensive toxic odors. Thus, when gingko leaves or Chinese herbal materials are treated with the SJP microorganisms according to the present invention, the toxicity of the gingko leaves or Chinese herbal materials can be reduced.

It was thought that, if ginkgo leaves are fermented and used as feed or feed additives for pigs, poultry and cattle, the medicinal component of the ginkgo leaves can be accumulated. Thus, ginkgo leaves were fermented in the following manner.

Ginkgo leaves were inoculated and fermented with each of 17 kinds of SJP microorganisms, dried and milled, thus preparing fermented ginkgo leaf compositions. *Sophora flavescens*, red pepper seed, licorice, cinnamon and *Scutellaria baicalensis* were diluted at the same amount, and inoculated with each of 17 kinds of microorganisms according to the present invention. Then the plants were placed in a heating cabinet maintained at 40° C. together with a control group non-inoculated with the inventive microorganisms, and were then fermented for 24 hours, thus preparing fermented Chinese herbal compositions. Among said fermented gingko leaf compositions, one composition fermented with yeast (SJP6844AF5) and two compositions fermented with *Bacillus* bacteria (SJP6734B4) were mixed with each other at the same ratio. The mixture was mixed with the composition fermented with yeast (SJP6732B2) among the fermented Chinese herbal compositions, at a mixing ratio of 1:1, thus preparing a Chinese herbal feed additive.

Each of the culture broth of the SJP microorganisms according to the present invention, and the Chinese herbal feed additive containing the fermented Chinese herbal composition and the gingko composition fermented with the SJP microorganism culture broth, were diluted in feed at a concentration of 1%. Chicken was fed with the feed, and the average body weight upon initiation of feeding and the average body weight gain after 8 days were examined.

As a result, the control group treated with the feed containing only the inventive SJP microorganism culture broth showed a body weight gain of about 400 g, but the group treated with the Chinese herb feed additive fermented with the SJP microorganism culture broth showed a body weight gain of about 600 g. Also, odors were not sensed at a distance of 2 m from the manure of all the treated livestock groups, and fly larvae were not substantially generated (50-100%) (Table 21).

Thus, it could be seen that when the feed additive obtained by fermenting ginkgo leaves and Chinese herbal materials with the SJP microorganism culture broth was fed, the growth of chicken was promoted; compared to when only the SJP microorganism culture broth according to the present invention was added to feed.

TABLE 21

Growth-promoting, odor-preventing and fly larva-preventing effects of SJP microorganisms and Chinese herb feed additives fermented with SJP microorganism culture broth

| | SJP culture broth (%) | Chinese herb feed additive (%) | Initial weight (g) | Final weight (g) | Bad smell | Fly larvae |
|---|---|---|---|---|---|---|
| SJP6728AF1 | 2 | 0 | 1410 | 1802 | NO | NO |
| SJP6729AF2 | 2 | 0 | 1415 | 1797 | NO | NO |
| SJP6730AF3 | 2 | 0 | 1439 | 1832 | NO | NO |
| SJP6740AF4 | 2 | 0 | 1418 | 1840 | NO | NO |
| SJP6744AF5 | 2 | 0 | 1444 | 1853 | NO | NO |
| SJP6726AF6 | 2 | 0 | 1420 | 1884 | NO | NO |
| SJP6743AF7 | 2 | 0 | 1489 | 1801 | NO | NO |
| SJP6728AF1 | 2 | 1 | 1497 | 2102 | NO | NO |
| SJP6730AF3 | 2 | 1 | 1445 | 2051 | NO | NO |
| SJP6740AF4 | 2 | 1 | 1433 | 1984 | NO | NO |

Example 10

Effect of Preventing Decomposition of Organic Material

In order to examine the decomposition-preventing effect on the organic material of 17 kinds of SJP microorganisms according to the present invention, bean curd was immersed in water, inoculated with each of said 17 kinds of SJP microorganisms, and left to stand at a temperature of 25-30° C. In the control group, odors began to be generated after 24 hours, but in all the groups treated with the SJP microorganisms, odors were not sensed up to 3 days. However, in the groups treated with the genus *Bacillus* among SJP microorganisms (SJP6722A5, SJP6731B1, SJP6735B6, SJP6844AF5, SJP6732B2, SJP6719B3, SJP6734B4, SJP6841L2, SJP6720L3 and SJP6742L5) except for yeasts, fine odors began to be generated from 4 days after the microbial treatment. After 5 days, some odors were generated in the yeast-treated groups, and after 7 days, severe odors were generated.

The bean curd was taken out of water, and the odor and tissue of the bean curd were examined. As a result, it could be seen that odors were generated on the surface of the bean curd, but the inner part of the bean curd was maintained intact, and the tissue and firmness of the bean curd were the same as the first stage.

Also, a mackerel was inoculated with each of 17 kinds of SJP microorganisms according to the present invention and left to stand at room temperature, and the odors thereof were examined. After 1 day, the control group generated offensive odors, and after 4 days, the groups treated with the genus *Bacillus* among SJP microorganisms (SJP6722A5, SJP6731B1, SJP6735B6, SJP6844AF5, SJP6732B2, SJP6719B3, SJP6734B4, SJP6841L2, SJP6720L3 and SJP6742L5) generated offensive odors. After 7 days, in the control group, fly larvae were generated. 7 days after the microbial treatment, all the groups treated with 7 kinds of yeasts (SJP6728AF1, SJP6729AF2, SJP6730AF3, SJP6840AF4, SJP6726AF6, SJP6843AF7 and SJP6723L4) among the SJP microorganism started to generate odors, and the groups treated with the genus *Bacillus* among SJP microorganisms began to generate fly larvae. However, the groups treated with the yeast among SJP microorganisms did not generate maggots even after 15 days. In the salted control group, some odors could be sensed after 15 days.

Soybeans were immersed in water for 2 hours, and then applied with each of 17 kinds of SJP microorganism culture broth according to the present invention. The treated groups and the control group were left to stand at a temperature of 20-25° C. As a result, the control group began to generate mold and odor after 5 days. After 20 days, the groups treated with the genus *Bacillus* among SJP microorganisms (SJP6722A5, SJP6731B1, SJP6735B6, SJP6844AF5, SJP6732B2, SJP6719B3, SJP6734B4, SJP6841L2, SJP6720L3 and SJP6742L5) turned black and, at the same time, showed a decomposition phenomenon, but had no offensive odor. However, the groups treated with the yeast among SJP microorganisms (SJP6728AF1, SJP6729AF2, SJP6730AF3, SJP6840AF4, SJP6726AF6, SJP6843AF7 and SJP6723L4) maintained the original state for 42 days, and slowly turned brown and became black after 60 days.

Also, soybeans were immersed in water for 10 minutes so that the soybeans absorb water. Then, the feed additive powder prepared according to the method of Example 6 using the yeast among SJP microorganisms of the present invention was added to the soybeans at a ratio of 1:10 and left to stand. As a result, the soybeans maintained the original state even after 3 months. This suggests that the SJP microorganisms according to the present invention can be used as preservatives for crops, fruits, vegetables, fish and shellfish.

Example 11

Bean Sprout Cultivation Test

Each of 17 kinds of SJP microorganism culture broth according to the present invention was diluted in water, which was then watered to bean sprout, or each of the SJP microorganism culture broth was applied to bean sprouts 2-3 times a day when it is not the time for watering. As a result, in all the groups treated with the SJP microorganism culture broth, the growth of the bean sprouts was promoted without decomposition.

Example 12

Fermentation of Soybean, Crops and Beef Bone Broth and Preparation of Cheese Soybeans were steamed, inoculated with each of SJP6728AF1 and SJP6729AF2 according to the present invention, and fermented for 30 hours. Then, the fermented soybeans were dried and powdered, thus preparing an enzyme food supplement. Then, 50 persons over 50 years old were selected and allowed to eat the fermented soybean enzyme food.

As a result, the soybeans fermented with SJP6728AF1 and SJP6729AF2 resulted in a nutty taste and fragrance, like roasted soybean flour, and most of the test subjects answered that they did not sense offensive odors upon a fart and excretion for 30 days of ingestion of the fermented soybeans, and the fermented soybeans had excellent digestion promoting effect and recovery effect from fatigue (Table 22).

TABLE 22

| Effects of ingestion of soybean food fermented with SJP microorganisms | | | | | | |
|---|---|---|---|---|---|---|
| Promotion of digestion | Bad smell of gas | Bad smell of excrement | Constipation solution | Recovery from fatigue | Energizing effect | Diet |
| 100% | 80% | 70% | 90% | 90% | 60% | 30% |

Also, cereals, such as unpolished rice, barley, wheat, bean and sesame, were mixed with each other at the same ratio, steamed, and then inoculated with each of SJP6728AF1 and SJP6729AF2. Then, the mixture was fermented at 35-40° C. for 2 days, kneaded and made into enzyme pills. When the pills were administered into persons, they had effects on digestion promotion, removing fecal stasis and odor prevention.

Beef bone broth obtained by degrading beef bones such as beef feet in hot water was inoculated with each of the SJP microorganism culture broth according to the present invention and fermented for 2 days. As a result, the characteristic odor of beef bone broth disappeared, and the color thereof was clear.

Sterilized milk was inoculated with one or more selected from 17 kinds of SJP microorganisms according to the present invention, and then fermented for 12 hours. When purely white cheese was coagulated, it was dewatered and tasted. As a result, the cheese had a sour taste and nutty taste, which are characteristic of microbial fermentation, and it had effects on digestion promotion and odor prevention upon excretion. Also, the cheese was placed in a heating cabinet at 40° C., and after 2 days, yeasts were grown, but the taste of the cheese was not changed. In a conventional cheese preparation method, there are problems in that a large amount of offensive odors occur, and a fermentation process must be conducted for a long time; however, the cheese fermented using the SJP microorganisms according to the present invention had no offensive odor, and did not give a greasy taste even when it was eaten after coagulation. Also, the inventive cheese had a nutty taste.

Example 13

Preparation of Bean Curd

A bean extract obtained by steaming bean juice and removing bean curd dregs was adjusted to 40.5° C. and then inoculated with each of SJP6728AF1 and SJP6729AF2 culture-broth. Then, the bean extract was fermented at 40° C. for 12 hours, and soft bean curd was prepared therefrom. According to a conventional bean curd dewatering process, the soft bean curd was placed into a bag and dewatered for 6 hours while being pressed under a weight of about 10 kg, thus preparing bean curd. The bean curd thus prepared was tasted and, as a result, it had the same taste as that of conventional bean curd, but had a sour taste, indicating fermentation.

5 liters of the bean extract was added to 5 liters of raw milk, and the mixture was inoculated with the SJP microorganisms according to the present invention and fermented for 24 hours, thus preparing a fermented semi-solid product made of the cheese/bean curd mixture.

Chocolate was added to the bean extract, the mixture was fermented and, as a result, chocolate bean curd was produced which had no sour taste. A pine leaf extract was added to raw milk, the mixture was fermented and, as a result, a cheese having pine leaf fragrance was produced. Also, salt and peach drink was added to the bean extract, the mixture was fermented and, as a result, the resulting product had peach fragrance and had no sour taste. Accordingly, mugwort and green tea can be used as food materials capable of harmonizing the taste and fragrance of said bean curd and cheese, and thus the inventive microorganisms can be used in a significantly large range of applications.

The bean curd treated with the inventive SJP microorganisms, and conventional bean curd, were immersed in water and left to stand in a heating cabinet maintained at 40° C., and whether the bean curds were spoiled was examined. As a result, the conventional bean curd generated spoiled bean curd odors after 24 hours. However, the bean curd treated with the SJP microorganisms was not spoiled even after 5 days, and the surface thereof was covered with grown yeasts. Accordingly, it was expected that the decomposition prevention effect of the inventive SJP microorganisms would last for at least 10 days. Also, when the bean curd or cheese treated with the SJP microorganisms was stored in a refrigerator, the offensive odors generated in the refrigerator disappeared.

Example 14

Garlic Fermentation

To measure the fermentation efficiency of the SJP microorganisms according to the present invention, 5 kg of garlic was added to 30 liters of water, heated to 130° C. and then cooled to 30° C. The resulting garlic solution was inoculated with each of the SJP6728AF1 and SJP6729AF2 culture broth, and then left to stand at room temperature for 30 days. As a result, the garlic was fermented such that the odor thereof was not sensed.

Figure 5:
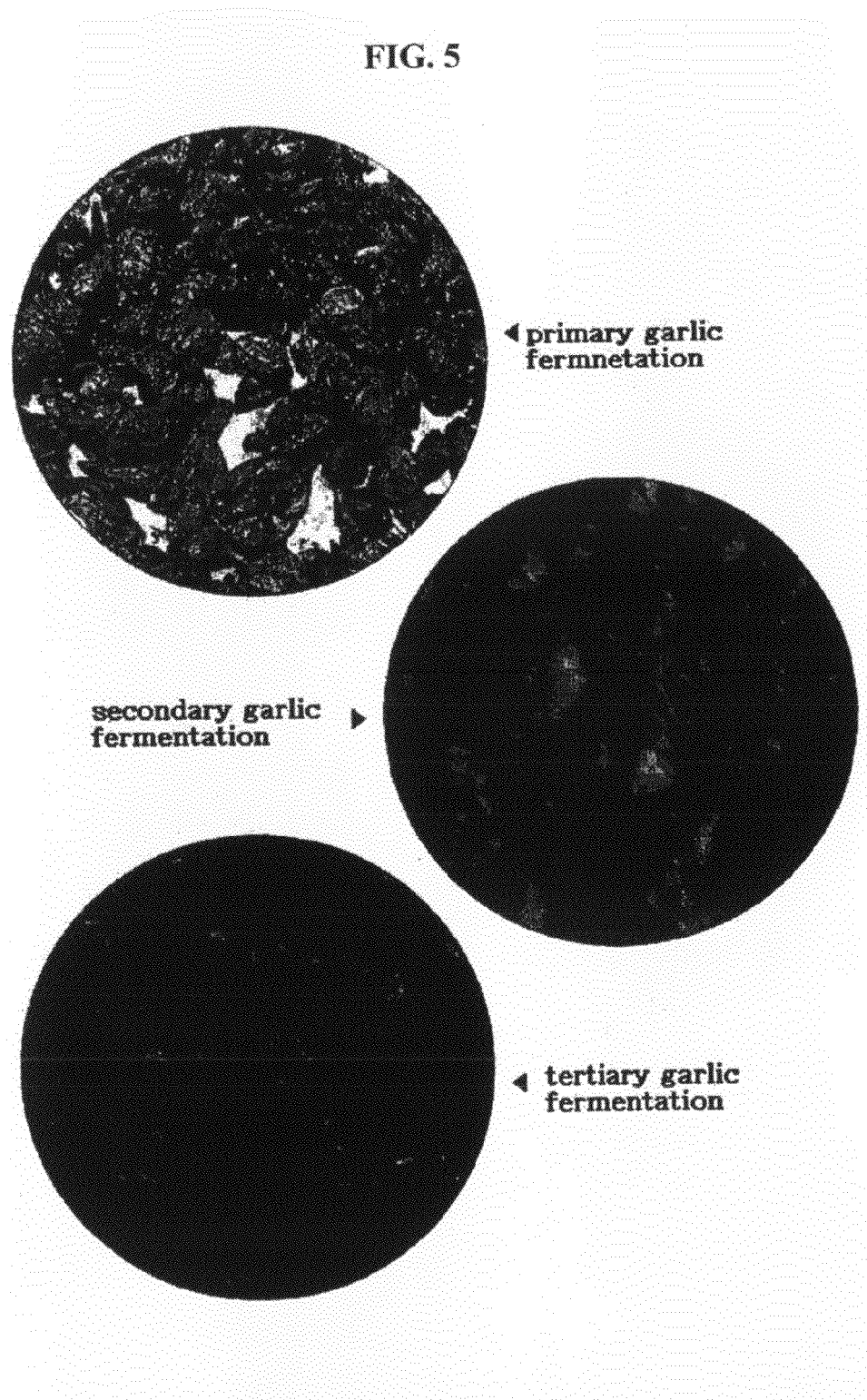
FIG. 5 shows photographs of garlic fermented using the microorganisms according to the present invention.

Garlic was steamed in a solid state and inoculated with each of the SJP6728AF1, SJP6729AF2 and SJP6731B1 culture broth. Then, the garlic was fermented at 35-40° C. for 2 days and dried for 2 days, and the fermentation and drying process was repeated three times. As a result, the garlic was turned red in primary fermentation, and black in secondary fermentation and tertiary fermentation (FIG. 5). The black garlic showed a reduction in the characteristic odor of garlic or the hot taste of allicin, and thus it is expected that the fermented enzyme of the garlic can be easily administered and be usefully used in cancer therapy.

Example 15

Ginseng Fermentation 300 g of ginseng powder obtained by drying and mining 6-year-old fresh ginseng was inoculated with each of the SJP microorganism culture broth according to the present invention and fermented at 35-40° C. for 10 days. The fermented ginseng was steamed and the components of the fermented ginseng were measured with HPLC.

The crude saponin content of the control group was 5.12 w/w %, and the Rb1 content thereof was 0.037 w/w %, whereas the crude saponin content of the fermented ginseng inoculated with the inventive SJP microorganism culture broth was 5 w/w %, and the Rb1 content thereof was 0.538 w/w % (Table 23). Table 24 shows the measurement results of the water content of fresh ginseng before and after treatment with the inventive SJP microorganism culture broth, and Table 25 shows the results of HPLC analysis of fresh ginseng.

TABLE 23

Components of ginseng fermented by SJP microorganisms

| Test item | Content (w/w %) |
|---|---|
| Crude saponin | 5.000 |
| Ginsenoside Rh2 | — |
| Rh1 | 0.538 |
| Rg2 | 1.111 |
| Rg3 | 1.769 |
| Rg1 | 11.212 |
| Rf | 2.338 |
| Re | 2.044 |
| Rd | — |
| Rc + Rb2 | 7.935 |
| Rb1 | 14.743 |

TABLE 24

Water content of fresh ginseng

| | Before treatment with SJP culture broth (g) | After treatment with SJP culture broth (g) | Water content (%) |
|---|---|---|---|
| Head | 0.635 | 0.165 | 74.0 |
| Major root | 9.592 | 2.999 | 68.7 |
| Rootlet | 4.046 | 1.268 | 68.7 |

TABLE 25

Results of HPLC analysis of fresh *ginseng*

| | Ethanol extract (g) | Crude saponin (%) | Total saponin (%) | Rb1/Rg1 | PD/PT | Ginseniside (w/w %) | | | | | | |
|---|---|---|---|---|---|---|---|---|---|---|---|---|
| | | | | | | Rb1 | Rb2 | Rc | Rd | Re | Rf | Rg |
| Total | 5.071 | 1.200 | 0.210 | 1.290 | 1.722 | 0.037 | 0.043 | 0.034 | 0.019 | 0.044 | 0.005 | 0.029 |
| Head | 0.149 | 1.888 | 0.218 | 1.309 | 1.526 | 0.047 | 0.043 | 0.030 | 0.012 | 0.045 | 0.005 | 0.036 |
| Major root | 3.423 | 0.737 | 0.055 | 0.929 | 0.964 | 0.010 | 0.007 | 0.007 | 0.002 | 0.012 | 0.004 | 0.011 |
| Rootlet | 1.192 | 1.477 | 0.296 | 2.737 | 2.325 | 0.059 | 0.068 | 0.050 | 0.030 | 0.063 | 0.004 | 0.022 |

This suggests that, when fresh ginseng inoculated with the SJP microorganisms according to the present invention is fermented, red ginseng extracts can be prepared in an amount more than two times larger than that of a conventional method for preparing red ginseng extracts. Particularly, even the fine root of the fresh ginseng fermented with the SJP6728AF1 or SJP6729AF2 culture broth could be prepared into red ginseng as shown in FIG. 6.

Example 16

Preparation of Rice Bran Beverage and Fermentation of Animal Extract and Fruit Juice An extract obtained by extracting rice bran at 121° C. was inoculated with each of the SJP6728AF1 and SJP6729AF2 culture broth and fermented for 48 hours. Then, the extract was sterilized and adjusted to a sugar content of 11.5-12.5% by adding sugar thereto, so that it had a sweet and sour taste and the characteristic fragrance of the SJP microorganisms, and thus another flavor did not need to be added thereto. However, when the extract was fermented after adding fragrant grass such as pine leaves, peppermints, herbs, lemons and green tea thereto, yeast beverages having various fragrances could be prepared, and when the yeasts were isolated and purified by centrifugation, enzyme beverages having an unchanged taste could be prepared.

Also, 8 kg of fresh-water eels, soft-shelled turtles, crucians, deer and snake fish were mixed with 500 g of licorice root, and the mixture was extracted, inoculated with SJP6728AF1, fermented for 2 days, and then sterilized at high temperature, thus preparing a food product. When the food was ingested, it provided an energy restoration effect.

Commercially available beverages made with oranges, pears, peaches, apples, carrots, tomatoes, pomegranates and grapes were purchased in the market and the sugar content and pH thereof were measured. The measurement results showed that the sugar content was 11.5-12.5%, and the pH was 3.3-3.8. The commercial beverages were inoculated with each of SJP6728AF1 and SJP6729AF2 and placed in a fermenter maintained at 35-40° C. After 24 hours of fermentation, the pH and sugar content of the fermented beverages were measured and, as a result, the pH was 3.3-3.8, which was the same as the pH of the non-fermented beverages, but the sugar content was 10-11.5%, which was about 1-1.5% lower than the sugar content of the non-fermented beverages. The fermented beverages were further fermented for 24 hours and the pH and sugar content thereof were measured and, as a result, the pH was not changed, but the sugar content was further decreased by about 2-3%. Also, the further fermented beverages smelled of alcohol and had a sour taste stronger than that of the 24 hours fermented beverages. The fermented beverages were sterilized by heating, were adjusted to a sugar content of 11.5-12.5% by adding sugar thereto, and were tasted. As a result, fruit beverages were prepared, in which fruit fragrance was stronger than that of the non-fermented beverages and which had a sweet taste together with a sour taste.

Example 17

Fermentation of Chinese Herbal Materials

In order to examine whether the bitter taste of Chinese herbal materials is changed when the Chinese herbal materials are fermented using the inventive SJP microorganisms, 500 g of *Phellinus liteus* was added to 15 liters of water and subjected to hot water extraction. The extract was inoculated with each of SJP6728AF1 and SJP6729AF2 and then placed in a fermenter maintained at 35-40° C. After 24 hours of fermentation, the extract was observed. As a result, a great amount of gas was generated, suggesting that the fermentation of the extract progressed. After 2 days of fermentation, the taste of the fermented extract was compared with the control group non-inoculated with the SJP microorganisms and, as a result, a bitter taste was not sensed in the SJP microorganism-treated group, but was maintained in the control group.

Also, Chinese herbs having high skin moisturizing effect, such as *Cnidium officinale, Angelica gigas Nakai*, and *Liriope platyphylla*, and animal protein such as eels, were inoculated with each of the SJP6728AF1 and SJP6729AF2 culture broth and fermented. Then, cosmetic materials such as ceramic powder were added thereto, and the mixture was massaged onto face for one week. As a result, the facial skin became soft, the face became bright, and a wrinkle improvement effect was shown.

Chinese herbs having effects against skin diseases, for example, *Sophora flavescens, Torilisjaponica* and *Scutellariae baicalensis*, were inoculated with each of the SJP6728AF1 and SJP6729AF2 culture broth and fermented. Then, whether the herbs can treat athlete's foot was examined, and, as a result, the athlete's foot was perfectly cured when the herbs were administered 2-3 times, and the athlete's foot did not recur for 5 months.

Chinese herbs such as *Scutellariae baicalensis* were inoculated with each of the SJP6728AF1 and SJP6729AF2 culture broth and fermented, thus preparing fermented solution. When the fermented broth was used as bathing water, it showed the effects of treating not only athlete's foot but also skin diseases, including atopic diseases.

Also, Chinese herbs such as *Pueraria lobata* and *Puerartia flos* were inoculated with each of the SJP6728AF1 and SJP6729AF2 culture broth and fermented, thus preparing beverages. When the beverages were ingested, they had an effect on removing hangover. *Chrysanthemum indicum* was inoculated with each of the SJP6728AF1 and SJP6729AF2 culture broth and fermented, thus preparing beverages. When the *Chrysanthemum indicum* beverages were ingested, they had the effects of removing headache pain and stabilizing blood pressure. An extract obtained by adding 6 kg of *Pueraria lobata* to 25 liters of water and subjecting the solution to hot water extraction was inoculated with each of the SJP6728AF1 and SJP6729AF2 culture broth and fermented for 5 days, and the sugar content thereof was measured. As a result, the sugar content was 5%. The fermented extract was adjusted to a sugar content of 10% by adding sugar thereto, and when it was ingested, it was effective at removing hangover.

3-year-old *Platycodon grandiflorum* solid was steamed, inoculated with each of the SJP6728AF1 and SJP6729AF2 culture broth and fermented for 2 days, and, as a result, the toxicity of the *Platycodon grandiflorum* disappeared. The *Platycodon grandiflorum* was fermented three times and dried three times, and thus it turned black. *Platycodon grandiflorum* has a problem in that it is not easily digested, but the black *Platycodon grandiflorum* can solve the problem of digestive absorption.

Example 18

Method of Fermenting Liquid Organic Material Absorbed into Solid Organic Material 300 g of *Saururus chinesis* and *Houttuynia cordata* were added to 3 liters of water, shaken for 2 hours, and then dewatered, thus obtaining 2 liters of a liquid organic material of *Saururus chinesis*. Soybeans were immersed in the above-prepared liquid organic material for 4 hours and, as a result, about 95% of the liquid organic material was absorbed into the soybeans. The resulting material was steamed, inoculated with the SJP6728AF1 culture broth, and fermented at 30° C.

for 48 hours. The fermented material was dried and milled, thus preparing a fermented composition. The fermented composition had low molecular weight, because the polymer components of *Saururus chinesis* were degraded by the microorganisms. Thus, the fermented composition has advantages in that the digestion efficiency thereof is increased and the nutrients of the fermented soybeans together with the microorganisms can be ingested.

Also, 300 g of fresh ginseng was added into 3 liters of water and subjected to hot water extraction, thus obtaining 2 liters of a liquid organic material of fresh ginseng. Black beans were immersed in the liquid organic material of fresh ginseng for 2 hours and, as a result, 90% of the liquid organic material was absorbed into the beans. The resulting material was steamed, inoculated with the SJP6729AF2 culture broth, fermented at 40° C. for 48 hours and then dried, thus preparing a fermented composition. When the fermented composition is ingested, the effects of the fermented ginseng occur and, at the same time, the low molecular weight soybean components can also be ingested.

1 liter of cereal powder obtained by crushing soybean, unpolished rice, *Phaseolus radiatus* and barley was mixed with 0.5 liters of a Chinese herb *Scutellaria baicalensis* extract and kneaded to obtain a semi-solid organic material. The semi-solid material was sterilized with water vapor, inoculated with the SJP6729AF2 microorganism culture broth, and then fermented at 30-40° C. for 60 hours, thus preparing a fermented composition. The Chinese herb *Scutellaria baicalensis* extract is a medicinal herb of alleviating jaundice caused by damp-heat and activating the function of liver and gall bladder, and has an antimicrobial effect of inhibiting the growth of *Pseudomonas aeruginosa, Shigella* sp., *E. coli, Bordetella pertussis*, skin fungi and the like. Thus, herbs having no antibacterial activity were completely fermented within 48 hours, and when the *Scutellaria baicalensis* was added thereto, the fermentation time was extended by 12 hours.

Black beans and black sesame were immersed in ShiQuanDaBuTang (hot water extract of ginseng, root of *Atractylodes japonica*, White poria cocos (Schw.) Wlof., licorice root, dried root of *Rehmannia glutinosa* Liboschitz var. *purpurea* Makino, *Paeonia japonica, Cnidium officinale, Angelica gigas* Nakai, *Astragalus membranaceus*, bark of *Cinnamomum cassia* Blume, date, and ginger) and steamed to prepare a semi-solid organic material. The semi-solid organic material was inoculated with the SJP6728AF1 culture broth and fermented for 3 days, thus preparing a fermented composition. As a result, the fermented composition obtained by inoculating the ShiQuanDaBuTang with the SJP6728AF1 culture broth and fermenting the inoculated material could have maximized potency, compared to when the ShiQuanDaBuTang was ingested in the form of a conventional hot water extract.

IINDUSTRIAL APPLICABILITY

As described in detail above, the inventive novel microorganisms having the efficiency of removing an odor from organic waste have the effects of preventing or removing the odor from organic waste and preventing the decomposition of organic waste, and thus improve an environment. Also, the inventive microorganisms have an insecticidal effect against noxious insects and an antifuingal effect against plant pathogenic fungi, can be used as feed additives and antibiotic substitutes, and also are useful for the preparation of fermented foods.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A live microorganism selected from the group consisting of a biologically pure culture of *Saccharomyces exiguus* SJP6728AF1 (KCCM-10675P) and a biologically pure culture of *Saccharomyces exiguus* SJP6729AF2 (KCCM-10677P).

2. A microbial agent for the fermentation of organic waste, which contains one or more live microorganisms selected from the group consisting of a biologically pure culture of *Saccharomyces exiguus* SJP6728AF1 (KCCM-10675P) and a biologically pure culture of *Saccharomyces exiguous* SJP6729AF2 (KCCM-10677P)in an amount effective for fermentation.

3. An agent for preventing or removing an offensive odor from organic waste, which contains one or more live microorganisms selected from the group consisting of a biologically pure culture of *Saccharomyces exiguus* SJP6728AF1 (KCCM-10675P) and a biologically pure culture of *Saccharomyces exiguus* SJP6729AF2 (KCCM-10677P) in an amount effective for preventing or removing an offensive oder from organic waste.

4. An insecticide, which contains one or more live microorganisms selected from the group consisting of a biologically pure culture of *Saccharomyces exiguus* SJP6728AF1 (KCCM-10675P) and a biologically pure culture of *Saccharomyces exiguus* SJP6729AF2 (KCCM-10677P)in an insecticidally effective amount.

5. A microbicide, which contains one or more live microorganisms selected from the group consisting of a biologically pure culture of *Saccharomyces exiguus* SJP6728AF1 (KCCM-10675P) and a biologically pure culture of *Saccharomyces exiguus* SJP6729AF2 (KCCM-10677P) in a microbicidally effective amount.

6. A preservative, which contains one or more live microorganisms selected from the group consisting of a biologically pure culture of *Saccharomyces exiguus* SJP6728AF1 (KCCM-10675P) and a biologically pure culture of *Saccharomyces exguus* SJP6729AF2 (KCCM-10677P) in a perservatively effective amount for crops, fruit, vegetables, fish, or shellfish.

7. A feed additive, which contains one or more live microorganisms selected from the group consisting of a biologically pure culture of *Saccharomyces exiguus* SJP6728AF1 (KCCM-10675P) and a biologically pure culture of *Saccharomyces exiguus* SJP6729AF2 (KCCM-10677P) in an amount effective as a feed additive.

8. A method for preparing a fermented food, the method comprises fermenting a food using one or more live microorganisms selected from the group consisting of a biologically pure culture of *Saccharomyces exiguus* SJP6728AF1 (KCCM-10675P) and a biologically pure culture of *Saccharomyces exiguus* SJP6729AF2 (KCCM-10677P) in an amount effective for food fermentation.

9. A fermented food prepared by the method of claim 8, which contains one or more live microorganisms selected from the group consisting of a biologically pure culture of *Saccharomyces exiguus* SJP6728AF1 (KCCM-10675P) and a biologically pure culture of *Saccharomyces exiguus* SJP6729AF2 (KCCM-10677P) in an amount effective for food fermentation.

10. A probiotic agent, which contains one or more live microorganisms selected from the group consisting of a biologically pure culture of *Saccharomyces exiguus* SJP6728AF1 (KCCM-10675P) and a biologically pure culture of *Saccharomyces exiguus* SJP6729AF2 (KCCM-10677P) in a probiotically effective amount.

* * * * *

SEQUENCE LISTING

<160> NUMBER OF SEQ ID NOS: 17

<210> SEQ ID NO 1
<211> LENGTH: 1699
<212> TYPE: DNA
<213> ORGANISM: Saccharomyces exiguus

<400> SEQUENCE: 1

```
ggccaagcgt tagttagcat ttatacgtga aactgcgaat ggctcattaa atcagttatc      60
gtttatttga tagttccttt actacatggt ataactgtgg taattctaga gctaatacat     120
gcttaaaatc tcgacctctg gaagagatgt atttattaga taaaaaatca atgtcttcgg     180
actctttgat gattcataat aacttttcga atcgcatggc cttgtgctgg cgatggttca     240
ttcaaatttc tgccctatca actttcgatg gtaggatagt ggcctaccat ggtttcaacg     300
ggtaacgggg aataagggtt cgattccgga gagggagcct gagaaacggc taccacatcc     360
aaggaaggca gcaggcgcgc aaattaccca atcctaattc acggaggtag tgacaataaa     420
taacgatacc gggcccattc gggtcttgca tttggaatga gtactatgta aataccttac     480
tgagcaatac tccgacgcca agtctgttgc cagcagccgc gaaaattcca gctccaatag     540
cgtatattaa agttgttgca gttaaaaagc tcgtagatga actttgagtc tgtttggccg     600
gcccgatttt tctccgtact ggcatcccaa gcggaccttt ccttctggct aaccttgggt     660
```

```
ccttgtggcc cctggcgaac caggattttt actttgaaaa aattagagtg ttcaaagcag    720
gcgtattgct cgaatatatt agcatggaat aatagaatag gacgtttggt tctattttgt    780
tggtttctag gaccatcgta atgattaata gggacggtcg ggggcatcag tattcaaatg    840
tcagaggtga aattcttgga tttttttgaag actaactact gcgaaagcat ttgccaagga   900
cgttttcatt aatcaagaac gaaagttagg ggatcgaaga tgatcagata ccgtcgtagt    960
cttaaccata aactatgccg actagggatc gggtggtgtt tttttaatga cccactcggc   1020
accttacgag aaatcaaagt ctttgggttc tgggggagt atggtcgcaa ggctgaaact    1080
taaaggaatt gacggaaggg caccaccagg agtggagcct gcggcttaat ttgactcaac   1140
acggggaaac tcaccaggtc cagacacaat aaggattgac agattgagag ctctttcttg    1200
attttgtggg tggtggtgca tggccgttat tagttggtgg agtgatttgt ctgcttaatt    1260
gcgataacga acgagacctt aacctactaa atagtggtgc tagcatttgc tggttgtcca   1320
cttcttagag ggactatcgg tttcaagccg atggaagttt gaggcaataa caggtctgtg   1380
atgcccttag acgttctggg ccgcacgcgc gctacactga cggagccagc gagtctaacc   1440
ttggccgaga ggtcttggta atcttgtgaa actccgtcgt gctggggata gagcattgta   1500
attattgctc ttcaacgagg aattcctagt aagcgcaagt catcagcttg cgttgattac    1560
gtccctgccc tttgtacaca ccgcccgtcg ctagtaccga ttgaatggct tagtgaggcc   1620
tcaggatctg cttagaggag ggggcaactc cacctcagag cggagaattt gacaaactgg   1680
tcatagagaa taatattgg                                                 1699

<210> SEQ ID NO 2
<211> LENGTH: 1693
<212> TYPE: DNA
<213> ORGANISM: Saccharomyces exiguus

<400> SEQUENCE: 2
ggggaaagag taagttagca tttatacagt gaaactgcga atggctcatt aaatcagtta     60
tcgtttattt gatagttcct ttactacatg gtataactgt ggtaattcta gagctaatac    120
atgcttaaaa tctcgacctc tggaagagat gtatttatta gataaaaaat caatgtcttc    180
ggactctttg atgattcata ataacttttc gaatcgcatg gccttgtgct ggcgatggtt    240
cattcaaatt tctgccctat caactttcga tggtaggata gtggcctacc atggtttcaa    300
cgggtaacgg ggaataaggg ttcgattccg gagagggagc ctgagaaacg gctaccacat    360
ccaaggaagg cagcaggcgc gcaaattacc caatcctaat tcagggaggt agtgacaata    420
aataacgata cagggcccat tcgggtcttg taattggaat gagtacgatg taaataccttt  480 aaccaggacc aattggccgg caagcctggt gccagcagcc gcggtaattc cagctccaat    540
agcgtatatt aaagttgttg cagttaaaaa gctcgtagtt gaactttggg tctgtttggc    600
cggtccgatt ttttcgtgta ctggaatccc aagcggacct ttccttctgg ctaaccttgg    660
gtccttgtgg ctcttggcga accaggattt ttactttgaa aaattagag tgttcaaagc    720 aggcgtattg ctcgaatata ttagcatgga ataatagaat aggacgtttg gttctatttt    780
gttggtttct aggaccatcg taatgattaa tagggacggt cggggcatc agtattcaaa    840 tgtcagaggt gaaattcttg attttttgaa agactaacta ctgcgaaagt atttgccaag    900
gacgttttca ttaatcaaga acgaaagtta ggggatcgaa gatgatcaga taccgtcgta    960
gtcttaacca taaactatgc cgactaggga tcggtggtg tttttttaat gacccactcg    1020
gcaccttacg agaaatcaaa gtctttgggt tctgggggga gtatggtcgc aaggctgaaa   1080
```

-continued

| | |
|---|---|
| cttaaaggaa ttgacggaag ggcaccacca ggagtggagc ctgcggctta atttgactca | 1140 |
| acacggggaa actcaccagg tccagacaca ataaggattg acagattgag agctctttct | 1200 |
| tgattttgtg ggtggtggtg catggccgtt cttagttggt ggagtgattt gtatgcttaa | 1260 |
| ttgcgataac gaacgaggcc ttaacctact aaatagtggt gctagcatgt gctggttgtc | 1320 |
| cacttcttag agggactatc ggtttcaagc cgatggaagt ttgaggcaat aacaggtctg | 1380 |
| tgatgcccTt agacgttctg gccgcacgc gcgctacact gacggagcca gcgagtctaa | 1440 |
| ccttggccga gaggtcttgg taatcttgtg aaactccgtc gtgctgggga tagagcattg | 1500 |
| taattattgc tcttcaacga ggaattccta gtaagcgcaa gtcatcagct tgcgttgatt | 1560 |
| acgtccctgc cctttgtaca caccgcccgt cgctagtacc gattgaatgg cttagtgagg | 1620 |
| cctcaggatc tgcttagagg aggggcaac tccacctcag agcggagaat ttgacaaact | 1680 |
| ggtcattaga gaa | 1693 |

<210> SEQ ID NO 3
<211> LENGTH: 1738
<212> TYPE: DNA
<213> ORGANISM: Candida fructus

<400> SEQUENCE: 3

| | |
|---|---|
| gtctcaaaga ttaagccatg catgtctaag tataagcaat ttatacagtg aaactgcgaa | 60 |
| tggctcatta aatcagttat cgtttatttg atagtacctt gctaattgga tatgcctggt | 120 |
| aattctagag ctaatacatg cgcacaagcc cgacctccgg aagggctgta tttattagat | 180 |
| aaaaaatcaa caccccgat gattcataat aacttgtcga atcgcatggc ctcgggccgg | 240 |
| cgatggttca ttcaaatttc tgccctatca actttcgatg gtaggataga ggcctaccat | 300 |
| ggtttcaacg ggtaacgggg aataagggtt cggttccgga gagggagcct gagaaacggc | 360 |
| taccacatcc aaggaaggca gcaggcgcgc aaattcccca atcccgacac ggggaggtag | 420 |
| tgacaataaa taacgatgca gggccttcg ggtcttgcaa ttggaatgag tacaatgtaa | 480 |
| ataccttaac gaggaacaat tggagggcaa gtctggtgcc agcagccgcg gtaattccag | 540 |
| ctccaagagc gtatattaaa gttgttgcag ttaaaaagct cgtagttgaa ccttggggag | 600 |
| gccgcgccgg tccgcgattt cgcgagcact ggaggcgggc ctcttacctc tctttggcgc | 660 |
| cctcgggcgg taaggagact gttactttga gaaaatgaga gtgttcaaag caggcgtacg | 720 |
| cttgaatctg ttagcatgga ataatagaat aggacgcatg gttctatttt gttggtttct | 780 |
| aggaccatcg taatgattaa tagggacggt cgggggcatc agtattcagt tgtcagaggt | 840 |
| gaaattcttg gatttactga agactaacta ctgcgaaagc atttgccaag gacgttttca | 900 |
| ttaatcaaga acgaaagtta ggggatcgaa gatgatcaga taccgtcgtg tctttaccat | 960 |
| aaactatact gactcgtgat cgggcggcgt tcatttagtg acgcgctcgg caccttacga | 1020 |
| gaaatcaaag tcttggttct gggatatcac gcctgggttc tgggggagt atggtcgcaa | 1080 |
| ggctgaaact taaaggaatt gacgaaggg caccaccagg agtggactgc ggcttaattt | 1140 |
| gactcaacac ggggaaactc accaggtcca gacacaataa ggattgacag attgagagct | 1200 |
| ctttcttgat tttgtgggtg gtggtgcatg gccgttctta gttggtggag tgatttgtct | 1260 |
| gcttaattgc gataacgaac gagaccttaa cctctaaata gggcgttagc attctgctgg | 1320 |
| cgcgcgcttc ttaggggac tattgacttg aagtcgatgg aagtttgagg caataacagg | 1380 |
| tctgtgatgc ccttagacgt tctgggccgc acgcgcgcta cactgacgga gccagcgagt | 1440 |
| tgaccttggc cgagaggtct gggaaatctt gggaaactcc gtcgtgctgg ggatagagca | 1500 |

```
ttgcaattgt tgctcttcaa cgaggaattc ctagtaagcg caagtcatca gcttgcgttg    1560
attacgtccc tgcccttttgt acacaccgcc cgtcgctact accgattgaa tggcttagtg   1620
aggcctccgg atttgtctaa gccgagggcg accttggact gtgacggaga agctggtcaa   1680
acttggtcat ttagaggaag taaaagtcgt aacaaggttt ccgtaggtga actgcgga     1738
```

<210> SEQ ID NO 4
<211> LENGTH: 1478
<212> TYPE: DNA
<213> ORGANISM: Lactobacillus paraplantarum

<400> SEQUENCE: 4

```
ccttctcgca gggcgtttat ctgcagtcga cgaactctg gtatgattgg tgcttgctca     60
tgaattacat ttgagtgagt ggcgaactgg tgacgtaaca cgtgggaaac ctgcccagaa   120 gcggggata acacctggaa acagatgcta ataccgcata acaacttgga ccgcatggtc    180
cgagtttgaa agatggcttc ggctatcact tttggatggt cccgcggcgt attagctaga   240
tggtgaggta acggctcacc atggcaatga tacgtagccg acctgagagg gtaatcggcc   300
acattgggac tgagacacgg cccaaactcc tacgggaggc agcagtaggg attttttccac  360 aatggacgaa attttgatgg agcaacgccg cgtgagtgaa gaaggggttttc ggctcgtaaa  420 actctgttgt taaagaagaa catatttgag agtaactgtt caggtattga cggtatttaa   480
ccagaaagcc acggctaact acgtgccagc agccgcggta atacgtaggt ggcaagcgtt   540
gtccggattt attgggcgta aagcgagcgc aggcggtttt ttaagtctga tgtgaaagcc   600
ttcggctcaa ccgaagaagt gcatcggaaa ctggggaact tgagtgcaga gaggacagt    660 ggaactccat gtgtagcggt gaaatgcgta gatatatgga agaacaccag tggcgaaggc   720
ggctgtctgg tctgtaactg acgctgaggc tcgaaagtat gggtagcaaa caggattaga   780
taccctggta gtccataccg taaacgatga atgctaagtg ttggagggtt ccgcccttc    840 agtgctgcag ctaacgcatt aagcattccg cctggggagt acggccgcaa ggctgaaact   900
caaaggaatt gacgggggcc cgcacaagcg gtggagcatg tggtttaatt cgaagctacg   960
cgaagaacct taccaggtct tgacatacta tgcaaatcta agagattaga cgttcccttc   1020
ggggacatgg atacaggtgg tgcatggttg tcgtcagctc gtgtcgtgag atgttgggtt   1080
aagtcccgca acgagcgcaa cccttattat cagttgccag cattaagttg ggcactctgg   1140
tgagactgcc ggtgacaaac cggaggaagg tggggatgac gtcaaatcat catgccccggt  1200 atgacctggg ctacactcgt gctacaatgg atggtacaac gagttgcgaa ctcgcgagag   1260
taagataatc tcttaaagcc attctcagct tcggattgta ggctgcaact tgcctacatg   1320
aagtcggaat tgcttgtaat cgcggatcag cattccgcgg tgaatacgtt cccgggcctt   1380
gacactccgc ccgtcactcc atgagagttt gtaacaccca agtcggtgg ggtgacgtta   1440 ttgaaccatg ccgcctacgt gacgattgtg aaagcaaa                           1478
```

<210> SEQ ID NO 5
<211> LENGTH: 1445
<212> TYPE: DNA
<213> ORGANISM: Bacillus badius

<400> SEQUENCE: 5

```
cccttgaggg gctacgcagt cagcggatga cggaagcttg cttccgttca agttagcggc    60
ggacgggtga gtaacacgtg gtaacctgc ctgtaagact gggataactc cgggaaaccg    120
gggctaatac cggatattct ttttcttcgc atgaagaaga atggaaaggc ggcttttagc   180
```

-continued

```
tgtcacttac agatggaccc gcggcgcatt agctagttgg tgaggtaacg gctcaccaag      240
gcaacgatgc gtagccgacc tgagagggtg atcggccaca ctgggactga gacacggccc      300
agactcctac gggaggcagc agtagggaat cttccgcaat ggacgaaagt ctgacggagc      360
aacgccgcgt gagtgaagaa ggttttcgga tcgtaaagct ctgttgtcag ggaagaacaa      420
gtacggaagt aactgtccgt accttgacgg tacctgacca gaaagccacg gctaactacg      480
tgccagcagc cgcggtaata cgtaggtggc aagcgttgtc cggaattatt gggcgtaaag      540
cgcgcgcagg cggcttctta agtctgatgt gaaagcccac ggctcaaccg tggagggtca      600
ttggaaactg ggaggcttga gtgcagaaga ggagagcgga attccacgtg tagcggtgaa      660
atgcgtagag atgtggagga acaccagtgg cgaaggcggc tctctggtct gtaactgacg      720
ctgaggcgcg aaagcgtggg gagcgaacag gattagatac cctggtagtc cacgccgtaa      780
acgatgagtg ctaagtgttg gagggtttcc gcccttcagt gctgcagcta acgcattaag      840
cactccgcct ggggagtacg gccgcaaggc tgaaactcaa aggaattgac ggggcccgc       900 acaagcggtg gagcatgtgg tttaattcga agcaacgcga agaaccttac caggtcttga      960
catcccgctg accggtctgg agacaggcct ttcccttcgg ggacagcggt gacaggtggt     1020
gcatggttgt cgtcagctcg tgtcgtgaga tgttgggtta agtcccgcaa cgagcgcaac     1080
ccttgatctt agttgccagc attcagttgg gcactctaag gtgactgccg gtgacaaacc     1140
ggaggaaggt ggggatgacg tcaaatcatc atgccccttta tgacctgggc tacacacgtg     1200
ctacaatgga tggtacaaag ggctgcaaga ccgcaaggtt tagccaatcc cataaaacca     1260
ttctcagttc ggattgcagg ctgcaactcg cctgcatgaa gccggaatcg ctagtaatcg     1320
cggatcagca tgccgcggtg aatacgttcc cgggccttgt acacaccgcc cgtcacacca     1380
cgagagtttg caacacccga gtcggtgggg taaccctac ggagccgccg ctaagtggca     1440
atggc                                                                 1445
```

<210> SEQ ID NO 6
<211> LENGTH: 1445
<212> TYPE: DNA
<213> ORGANISM: Paenibacillus polymyxa

<400> SEQUENCE: 6

```
ggttcggagg gggtctatac tgcagtgagc ggggttgttt agaagcttgc ttctaattaa       60
cctagcggcg gacgggtgag taacacgtag gcaacctgcc cacaagacag ggataactac      120
cggaaacggt agctaatacc cgatacatcc ttttcctgca tgggagaagg aggaaaggcg      180
gagcaatctg tcacttgtgg atgggcctgc ggcgcattag ctagttggtg ggtaatggc       240 ctaccaaggc gacgatgcgt agccgacctg agagggtgat cggccacact gggactgaga      300
cacggcccag actcctacgg gaggcagcag tagggaatct tccgcaatgg cgaaagcct       360 gacggagcaa cgccgcgtga gtgatgaagg ttttcggatc gtaaagctct gttgccaggg      420
aagaacgtct tgtagagtaa ctgctataag agtgacggta cctgagaaga agccccggc      480 taactacgtg ccagcagccg cggtaatacg taggggcaa gcgttgtccg gaattattgg      540
gcgtaaagcg cgcgcaggcg gctctttaag tctggtgttt aatcccgagg ctcaacttcg      600
ggtcgcactg gaaactgggg agcttgagtg cagaagagga gagtggaatt ccacgtgtag     660
cggtgaaatg cgtagagatg tggaggaaca ccagtggcga aggcgactct ctgggctgta     720
actgacgctg aggcgcgaaa gcgtggggag caaacaggat tagataccct ggtagtccac     780
gccgtaaacg atgaatgcta ggtgttaggg gtttcgatac ccttggtgcc gaagttaaca     840
```

```
cattaagcat tccgcctggg gagtacggtc gcaagactga aactcaaagg aattgacggg      900
gacccgcaca agcagtggag tatgtggttt aattcgaagc aacgcgaaga accttaccag      960
gtcttgacat ccctctgacc gctgtagaga tatggctttc cttcgggaca gaggagacag     1020
gtggtgcatg gttgtcgtca gctcgtgtcg tgagatgttg ggttaagtcc cgcaacgagc     1080 gcaacccta tgcttagttg ccagcaggtc aagctgggca ctctaagcag actgccggtg     1140
acaaaccgga ggaaggtggg gatgacgtca atcatcatg ccccttatga cctgggctac      1200
acacgtacta caatggccgg tacaacggga agcgaagccg cgaggtggag ccaatcctag     1260
aaaagccggt ctcagttcgg attgcaggct gcaactcgcc tgcatgaagt cggaattgct     1320
agtaatcgcg gatcagcatg ccgcggtgaa tacgttcccg ggtcttgtac acaccgcccg     1380
tcacaccacg agagtttaca acacccgaag tcggtgagga accgcaaggg ccgccccaag     1440
tggaa                                                                 1445

<210> SEQ ID NO 7
<211> LENGTH: 1699
<212> TYPE: DNA
<213> ORGANISM: Candida zeylanoides

<400> SEQUENCE: 7
ggcgtcgagt aagttagcat ttatacagtg aaactgcgaa tggctcatta aatcagttat       60
cgtttatttg atagtacctt tactacttgg ataaccgtgg taattctaga gctaatacat      120
gctaaaaatc ccgacttctg gaagggatgt atttattaga taaaaaatca atgctcttcg      180
gagctctttg atgattcata ataacttttc gaatcgcatg gccttgtgct ggcgatggtt      240
cattcaaatt tctgccctat caactttcga tggtaggata gtggcctacc atggtttcaa      300
cgggtaacgg ggaataaggg ttcgattccg gagagggagc ctgagaaacg gctaccacat      360
ccaaggaagg cagcaggcgc gcaaattacc caatcccgac acggggaggt agtgacaata      420
aataacgata cagggcccct tcgggtcttg taattggaat gagtacaatg taaataccct      480
aacgaggaac aattggaggg caagtctggt gtcaccagcc gccgtaattc cagctccaat      540
agcgtatatt aaagttgttg cagttaaaaa gctcgtagtt gaaccttggg cttggttggc      600
cggtccgctt tatggcgagt actgacccca accgagcctt tccttctggc taaccattcg      660
cccttgtggt gtttggcgaa ccaggacttt tactttgaaa aaattagagt gttcaaagca      720
ggcctttgct cgaatatatt agcatggaat aatagaatag gacgttatgg ttctattttg      780
ttggtttcta cgaccatcgt aatgattaat acggacggtc gggggcatca gtattcagtt      840
gtcagaggtg aaattcttgg atttactgaa gactaactac tgcgaaagca tttgccaagg      900
acgttttcat taatcaagaa cgaaagttag gggatcgaag atgatcagat accgtcgtag      960
tcttaaccat aaactatgcc gactaggat cgggtgttgt tcttttttg acgcactcgg      1020 caccttacga gaaatcaaag tctttgggtt ctgggggag tatggtcgca aggctgaaac     1080
ttaaaggaat tgacggaacg gcaccaccag gagtggagcc tgcggcttaa tttgactcaa     1140 cacgggaaa ctcaccaggt ccagacacaa taaggattga cagattgaga gctctttctt     1200
gattttgtgg gtggtggtgc atggccgttt cttagtaggg ggagtgattt gtctgcttaa     1260
ttgcgataac gaacgagacc ttaacctact aaatagtgct gctagctttt gctggtatag     1320
tcacttctta gagggactat cgatttcaag tcgatggaag tttgaggcaa taacaggtct     1380
gtgatgccct tagacgttct gggccgcacg cgcgctacac tgacggagcc agcgagttcc     1440
aaccttggcc gagaggtctg ggtaatcttg tgaaactccg tcgtgctggg gatagagcat     1500
```

```
tgtaattatt gctcttcaac gaggaattcc tagtaagcgc aagtcatcag cttgcgttga    1560
ttacgtccct gcccttttgta cacaccgccc gtcactacta ccgattgaat ggcttagtga   1620
ggcttccgga ttggtttaaa gaaggggggca acctcatctg gaacgaaaag cagtcaaact   1680
ggtcatagga agcatatgc                                                 1699

<210> SEQ ID NO 8
<211> LENGTH: 1730
<212> TYPE: DNA
<213> ORGANISM: Candida zeylanoides

<400> SEQUENCE: 8
gggggatacc ggcatgctct atgtataagc aatttataca gtgaaactgc gaatggctca      60
ttaaatcagt tatcgtttat ttgatagtac ctttactact tggataaccg tggtaattct     120
agagctaata catgctaaaa atcccgactt ctggaaggga tgtatttatt agataaaaaa     180
tcaatgctct tcggagctct ttgatgattc ataataactt ttcgaatcgc atggccttgt     240
gctggcgatg gttcattcaa atttctgccc tatcaacttt cgatggtagg atagtggcct     300
accatggttt caacgggtaa cggggaataa tgtttctatt ccggacacgg agcctgagaa     360
acggctacca catccaagga aggcagcagg cgcgcaaatt acccaatccc gacacgggga     420
ggtagtgaca ataaataacg atacagggcc ctttcgggtc ttgtaattgg aatgagtaca     480
atgtaaatac cttaacgagg aacaattgga gggcaagtct ggtgccagca gccgcggtaa     540
ttccagctcc aatagcgtat attaaagttg ttgcagttaa aaagctcgta gttgaacctt     600
gggcttggtt ggccggtccg ctttatggcg agtactggac ccaaccgagc ctttccttct     660
ggctaaccat tcgcccttgt ggtgtttggc gaaccaggac ttttactata aaaaaattag     720
attgttcaaa gcaggccttt gctcgaatat attagcatgg aataatagaa taggacgtta     780
tggttctatt ttgttggttt ctaggaccat cgtaatgatt aatagggacg tcgggggca     840 tcagtattca gttgtcagag gtgaaattct tggatttact gaagactaac tactgcgaaa     900
gcatttgcca aggacgtttt cattaatcaa gaacgaaagt taggggatcg aagatgatca     960
gataccgtcg tagtcttaac cataaactat gccgactagg gatcgggtgt tgttctttt    1020 ttgacgcact cggcacctta cgagaaatca aagtctttgg ttctgggggg agtatggtcg   1080
caaggctgaa acttaaagga attgacggaa cggcaccacc aggagtggag cctgcggctt   1140
aatttgactc aacacgggga aactcaccag gtccagacac aataaggatt gacagattga   1200
gagctctttc ttgattttgt gggtggtggt gcatggccgt tcttagttgg tggagtgatt   1260
tgtctgctta attgcgataa cgaacgagac cttaacctac taaatagtgc tgctagcttt   1320
tgctggtata gtcacttctt agagggacta tcgatttcaa gtcgatggaa gtttgaggca   1380
ataacaggtc tgtgatgccc ttagacgttc tgggccgcac gcgcgctaca ctgacggagc   1440
cagcgagttc taaccttggc cgagaggtct gggtaatctt gtgaaactcc gtcgtgctgg   1500
ggatagagca ttgtaattat tgctcttcaa cgaggaattc ctagtaagcg caagtcatca   1560
gcttgcgttg attacgtccc tgcccttttgt acacaccgcc cgtcactact accgattgaa   1620
tggcttagtg aggcttccgg attggtttaa agaaggggggg caacctcatc tggaactgaa   1680
aagctagtca aacttggtca tttagaggaa gtacaagtcg taacaaggtt             1730

<210> SEQ ID NO 9
<211> LENGTH: 1710
<212> TYPE: DNA
<213> ORGANISM: Kazachstania aerobia
```

<400> SEQUENCE: 9

```
ttcgtcagag taagttagca tttatacagt gaaactgcga atggctcatt aaatcagtta    60
tcgtttattt gatagttcct ttactacatg gtataactgt ggtaattcta gagctaatac   120
atgcttaaaa tcccgacctt ttggaaggga tgtatttatt agataaaaaa tcaatgtctt   180
cggactcttt gatgattcat aataactttt cgaatcgcat ggccttgtgc cggcgatggt   240
tcattcaaat ttctgcccta tcaactttcg atggtaggat agtggcctac catggtttca   300
acgggtaacg gggaataagg gttcgattcc ggagagggag cctgagaaac ggctaccaca   360
tccaaggaag gcagcaggcg cgcaaattac ccaatcctaa taccgggagg tagtgacaat   420
aaataacgat accgggccct ttcgggtcct gtaattggaa tgactacaat gtaaatacct   480
taacgaggaa caattggagg gcaagtctgg tgccagcagc cgcggtaatt ccagctccaa   540
tagcgtatat taagttgtt gcagttaaaa agctcgtagt tgaactttgg gcctggttgg   600
ccggtctggc tttttgccgc gtaatgtaat gctacgggc ctgtcgttgt ggctaacctt    660
aggctcgtgg tgggtctttg gcgaaccagg acttttactt tgaaaaaatt agagtgttca   720
aagcaggcgt attgctcgaa tatattagca tggaataatg gaataggacg tttggttcta   780
ttttgttggt ttctaggacc atcgtaatga ttaataggga cggtcggggg catcagtatt   840
caattgtcag aggtgaaatt cttggattta ttgaagacta actactgcga aagcatttgc   900
caaggacgtt ttcattaatc aagaacgaaa gttagggggat cgaagatgat cagataccgt   960
cgtagtctta accataaact atgccgacta gggatcgggt ggtgttttt taatgaccca   1020
ctcggcacct tacgagaaat caaagtcttt gggttctggg gggagtatgg tcgcaaggct  1080
gaaacttaaa ggaattgacg gaagggcacc accaggagtg gagcctgcgg cttaatttga  1140
ctcaacacgg ggaaactcac caggtccaga cacaataagg attgacagat tgagagctct  1200
ttcttgattt tgtgggtggt ggtgcatggc cgttcttagt tggtggagtg atttgtctgc  1260
ttaattgcga taacgaacga gaccttaacc tactaaatag tggtgctagc atttgctggt  1320
tcttccactt cttagaggga ctatcgattt caagtcgatg gaagtttgag gcaataacag  1380
gtctgtgatg cccttagacg ttctgggccg cacgcgcgct acactgacgg agccagcgag  1440
tctaacctag gccgagaggt cctggtaatc ttgtgaaact ccgtcgtgct ggggatagag  1500
ctttgtaatt tttgctcttc aacgaggaat tcctagtaag cgcaagtcat cagcttgcgt  1560
tgattacgtc cctgcccttt gtacacaccg cccgtcgcta gtaccgattg aatggcttag  1620
tgaggcctca ggatctgctt agagaagggg gcaactccat ctcagagcgg aaaatctggt  1680
caaactggtc atagagaata atatacgtgg                                    1710
```

<210> SEQ ID NO 10
<211> LENGTH: 1682
<212> TYPE: DNA
<213> ORGANISM: Candida humilis

<400> SEQUENCE: 10

```
ggcgtcgctg cagttagcat ttatacgtga aactgcgaat ggctcattaa atcagttatc    60
gtttatttga tagttccttt actacatggt ataactgtgg taattctaga gctaatacat   120
gcttaaaatc tcgacctctg aagagatgt atttattaga taaaaaatca atgtcttcgg   180
actctttgat gattcataat aacttttcga atcgcatggc cttgtgctgg cgatggttca   240
ttcaaatttc tgccctatca actttcgatg gtaggatagt ggcctaccat ggtttcaacg   300
ggtaacgggg aataagggtt cgattccgga gagggagcct gagaaacggc taccacatcc   360
```

-continued

```
aaggaaggca gcaggcgcgc aaattaccca atcctaaatc ccggaggtag tgacaataaa      420
taacgataca gggcccattc gggtcttgta attggaatga gtacaatgta aataccttaa      480
cgaggaacaa ttggagggca agtctggtgc cagcagccgc ggtaattcca gctccaatag      540
cgtatattaa agttgttgca gttaaaaagc tcgtagttga actttgggtc tgtttggccg      600
gtccgatttt ttcgtgtact ggaatcccaa gcggaccttt ccttctggct aaccttgggt      660
ccttgtggct cttggcgaac caggattttt actttgaaaa aattagagtg ttcaaagcag      720
gcgtattgct cgaatatatt agcatggaat aatagaatag gacgtttggt tctattttgt      780
tggtttctag gaccatcgta atgattaata gggacggtcg ggggcatcag tattcaaatg      840
tcagaggtga aattcttgga tttttttgaag actaactact gcgaaagcat tgccaaggat       900
cgttttcatt aatcaagaac gaaagttagg ggatcgaaga tgatcagata ccgtcgtagt      960
cttaaccata aactatgccg actagggatc gggtggtgtt ttttaatga cccactcggc       1020 accttacgag aaatcaaagt ctttgggttc tgggggagt atggtcgcaa ggctgaaact       1080
taaaggaatt gacggaaggg caccaccagg agtggagcct gcggcttaat ttgactcaac      1140
acggggaaac tcaccaggtc cagacacaat aaggattgac agattgagag ctctttcttg      1200
attttgtggg tggtggtgca tggccgttct tagttggtgg agtgatttgt ctgcttaatt      1260
gcgataacga acgagacctt aacctactaa atagtggtgc tagcatttgc tggttgtcca      1320
cttcttagag ggactatcgg tttcaagccg atggaagttt gaggcaataa caggtctgtg      1380
atgcccttag acgttctggg ccgcacgcgc gctacactga cggagccagc gagtctaacc      1440
ttggccgaga ggtcttggta atcttgtgaa actccgtcgt gctgggata gagcattgta       1500 attattgctc ttcaacgagg aattcctagt aagcgcaagt catcagcttg cgttgattac      1560
gtccctgccc tttgtacaca ccgcccgtcg ctagtaccga ttgaatggct tagtgaggcc      1620
tcaggatctg cttagaggag ggggcaactc caccctcagag cggagaattt gacaaactgt      1680
ca                                                                     1682
```

<210> SEQ ID NO 11
<211> LENGTH: 1463
<212> TYPE: DNA
<213> ORGANISM: Paenibacillus lactis

<400> SEQUENCE: 11

```
gggagctgcg gcgtgctata ctgcaagtcg agcggagttg atggagtgct tgctctcctg       60
atgcttagcg gcggacgggt gagtaacacg taggcaacct gccctcaaga ctgggataac      120
taccggaaac ggtagctaat accggataat taaattcgct gcatggcgga tttatgaaag      180
gcggagcaat ctgtcacttg aggatgggcc tgcggcgcat tagctagttg gtgaggtaac      240
ggctcaccaa ggcgacgatg cgtagccgac ctgagagggt gaacggccac gctgggactg      300
acacacggcc cagactccta cgggaggcag cagtacggaa tcttccgcaa tgggcgaaag      360
cctgacggag caacgccgcg tgagtgatga aggttttcgg atcgtaaagc tctgttgcca      420
gggaagaacg tctcatagag taactgctat gagagtgacg gtacctgaga agaaagcccc      480
ggctaactac gtgccagcag ccgcggtaat acgtagggg caagcgttgt ccggaattat      540
tgggcgtaaa gcgcgcgctg gcggttcttt aagtctggtg tttaaacccg aggctcaact      600
tcgggacgca ctggaaactg gggaacttga gtgcagaaga ggagagtgga attccacgtg      660
tagcggtgaa atgcgtagat atgtggagga acaccagtgg cgaaggcgac tctctgggct      720
gtaactgacg ctgaggcgcg aaagcgtggg gagcgaacag gattagatac cctggtagtc      780
```

```
cacgccgtaa acgatgaatg ctaggtgtta ggggtttcga tacccttggt gccgaagtta    840
acacattaag cattccgcct ggggagtacg gtcgaagact aaaaataaaa gaaattaccg    900
gggaccggcc caaacagtgg agtatgtggt ttaattagaa gcaacgcgaa gaaccttacc    960
aagtcttgac atccttctga atcctataga gatagaggcg gccttcggga cagaggagac   1020
aggtggtgca tggttgtcgt cagctcgtgt cgtgagatgt tgggttaagt cccgcaacga   1080
gcgcaaccct tgatcttagt tgccagcact ttgggtgggc actctaaggt gactgccggt   1140
gacaaaccgg aggaaggtgg ggatgacgtc aaatcatcat gccccttatg acttgggcta   1200
cacacgtact acaatggctg gtacaacggg aagcgaagcc gcgaggtgga gccaatccta   1260
aaaagccagt ctcagttcgg attgcaggct gcaactcgcc tgcatgaagt cggaattgct   1320
agtaatcgcg gatcagcatg ccgcggtgaa tacgttcccg ggtcttgtac acaccgcccg   1380
tcacaccacg agagtttaca cacccgaag tcggtggggt aaccctcacg ggagccagcc   1440
gccgaaggtg gtagagatgg tct                                          1463

<210> SEQ ID NO 12
<211> LENGTH: 1497
<212> TYPE: DNA
<213> ORGANISM: Paenibacillus sp. AY397772

<400> SEQUENCE: 12
gggcgacgtg cgcgtgctat actgcaagtc gagcggagct tagccttcct ttggaaggct     60
ctggcttagc ggcggacggg tgagtaacac gtaggcaacc tgcccgtaag accgggataa    120
cttgcggaaa cgtgagctaa taccggatag atgggaagag cgcatgctct cttaggaaa     180 gacggagcaa tctgtcactt acggatgggc ctgcggcgca ttagctagtt ggtggggtaa    240
aggcctacca aggcgacgat gcgtagccga cctgagaggg tgaccggcca cactgggact    300
gagacacggc ccagactcct acgggaggca gcagtaggga tcttcggca atggacggaa     360 gtctgaccga gcaacgccgc gtgagtgaag aaggttttcg gatcgtaaaa ctctgttgcc    420
agagaagaaa gctaaggaga gtcactgctc tttggttgac ggtatctgag aagaaagccc    480
cggctaacta cgtgccagca gccgcggtaa tacgtagggg gcaagcgttg tccggaatta    540
ttgggcgtaa agcgcgcgca ggcggctgag taagtctggt gtttaaacct ggggctcaac    600
ctcgggtcgc attggaaact gcttggctgg agtgcaggag aggaaagtgg aattccacgt    660
gtagcggtga aatgcgtaga gatgtggagg aacaccagtg gcgaaggcga ctttctggcc    720
tgtaactgac gctgaggcgc gaaagcgtgg ggagcaaaca ggattagata ccctggtagt    780
ccacgccgta aacgatgaat gctaggtgtc aggggtttcg ataccttggt gccgaagtt     840 aacacattaa gcattccgcc tggggagtac ggtcgcaaga ctgaaactca aggaattga    900 cggggacccg cacaagcagt ggagtatgtg gtttaattcg aagcaacgcg aagaaccta    960 ccaggtcttg acatccctct gaccgttcta gatagggc ttcccttcgg ggcagaggag   1020
acaggtggtg catggttgtc gtcagctcgt gtcgtgagat gttgggttaa gtcccgcaac   1080
gagcgcaacc cttgatctta gttgccagca ttgagttggg cactctagga tgactgccgg   1140
cgacaaaccg gaggaaggtg gggatgacgt caaatcatca tgccccttat gacctgggct   1200
acacacgtac tacaatggcc ggtacaacgg gcagcgaagc agcgatccgg agcgaatccc   1260
aaaaagccgg tctcagttcg gattgcaggc tgcaactcgc ctgcacgaag tcggaattgc   1320
tagtaatcgc ggatcagcat gccgcggtga atacgttccc gggtcttgta cacaccgccc   1380
gtcacaccac gaaagtttac aacacctgaa gtcggtgagg taaccctggt tgcagaacgt   1440
```
tgtttgcaga cataggagcc ccagccgccc cgacaggtgg ggggtacgat gattggg          1497

<210> SEQ ID NO 13
<211> LENGTH: 1452
<212> TYPE: DNA
<213> ORGANISM: Brevibacillus borstelensis

<400> SEQUENCE: 13
gcggcgtgcc taatacatgc aagtcgagcg agtcccttcg ggggctagcg gcggacgggt    60
gagtaacacg taggcaacct gcccgtaagc tcgggataac atggggaaac tcatgctaat   120
accggatagg gtcttctctc gcatgagagg agacggaaag gtggcgcaag ctaccactta   180
cggatgggcc tgcggcgcat tagctagttg gtggggtaac ggcctaccaa ggcgacgatg   240
cgtagccgac ctgagagggt gaccggccac actgggactg agacacggcc cagactccta   300
cgggaggcag cagtagggaa atttccccca atggacgaaa gttttgatgg agcaacgccg   360
cgtgaacgga tgaaggtctt tggattgtaa agttctgttg tcagagacga acaagttccg   420
tttgaacagg ggggtacctt gacggtacct gacgagaaag ccacggctaa ctacgtgcca   480
gcagccgcgg taatacgtag gtggcaagcg ttgtccggaa ttattgggcg taaagcgcgc   540
gcaggcggct atgtaagtct ggtgttaaag cccggggggtc aaccccggtt cgcatcggaa   600
actgggtagc ttgggagcag gagaggaaaa ggggaatgcg gtattaccgg tgtaacgggg   660
aaaggtgtgg agatgtggcg gaacaccagt ggggaaggcg gcttttggt ctgtaactga    720
cgctgaggcg cgaaagcgtg gggagcaaac aggattagat accctggtag tccacgccgt   780
aaacgatgag tgctaggtgt tgggggttc aataccctca gtgccgcagc taacgcaata    840
agcactccgc ctggggagta cgctcgcaag agtgaaactc aaaggaattg acggggcccc   900
gcacaagcgg tggagcatgt ggtttaattt gaagcaacgc gaagaacctt accaggtctt   960
gacatcccgc tgaccgtcct agagataggg cttcccttcg gggcagcggt gacaggtggt  1020
gcatggttgt cgtcagctcg tgtcgtgaga tgttgggtta agtcccgcaa cgagcgcaac  1080
ccttatcttt agttgccagc attcagttgg gcactctaga gagactgccg tcgacaagac  1140
ggaggaaggc ggggatgacg tcaaatcatc atgcccctta tgacctgggc tacacacgtg  1200
ctacaatggc tggtacaacg ggaagctagc tcgcgagagt atgccaatct cttaaaacca  1260
gtctcagttc ggattgcagg ctgcaactcg cctgcatgaa gtcggaatcg ctagtaatcg  1320
cggatcagca tgccgcggtg aatacgttcc cgggccttgt acacaccgcc cgtcacacca  1380
cgggagtttg caacacccga agtcggtgag gtaaccgcca aggagccagc cgccgaaggt  1440
ggtagagaag gg                                                       1452

<210> SEQ ID NO 14
<211> LENGTH: 1491
<212> TYPE: DNA
<213> ORGANISM: Lactobacillus casei

<400> SEQUENCE: 14
gggggactgc gggtgctata ctgcaagtcg aacgagttct cgttgatgat cggtgcttgc     60
accgagattc aacatggaac gagtggcgga cgggtgagta acacgtgggt aacctgccct   120
taagtggggg ataacatttg gaaacagatg ctaataccgc atagatccaa gaaccgcatg   180
gttcttggct gaaagatggc gtaagctatc gcttttggat ggacccgcgg cgtattagct   240
agttggtgag gtaatggctc accaaggcga tgatacgtag ccgaactgag aggttgatcg   300
gccacattgg gactgagaca cggcccaaac tcctacggga ggcagcagta gggaatcttc   360

```
cacaatggac gcaagtctga tggagcaacg ccgcgtgagt gaagaaggct ttcgggtcgt    420
aaaactctgt tgttggagaa aaaggacgt aagaggaact gatgtcggcg tgacggtatc    480
ctaaccagaa agccacggct aaactacgtg ccagcagccg cggtaatacg taggtggcaa    540
gcattatccg gatttattgg gcgtaaagcg agcgcaggcg gttttttaag tctgatgtga    600
aagccctcgg cttaaccgag gaagcgcatc ggaaactggg aaacttgagt gcagaagagg    660
acagtggaac tccatgtgta gcggtgaaat gcgtagatat atggaagaac accagtggcg    720
aaggcggctg tctggtctgt aactgacgct gaggctcgaa agcatgggta gcgaacagga    780
ttagataccc tggtagtcca tgccgtaaac gatgaatgct aggtgttgga gggtttccgc    840
ccttcagtgc cgcagctaac gcattaagca ttccgcctgg ggagtacgac cgcaaggttg    900
aaactcaaag gaattgacgg gggcccgcac aagcggtgga catgtggtt taattcgaag    960 caacgcgaag aaccttacca ggtcttgaca tcttttgatc acctgagaga tcaggtttcc   1020
ccttcggggg caaaatgaca ggtggtgcat ggttgtcgtc agctcgtgtc gtgagatgtt   1080
gggttaagtc ccgcaacgag cgcaaccctt atgactagtt gccagcattt agttgggcac   1140
tctagtaagg cagccggaga caaaccggag gaaggtgggg atgacgtcaa atcatcatgc   1200
cccttatgac atgggctaca cacgtgctac aatggatggt acaacgagtt gcgagaccgc   1260
gaggtcaagc taatctctta aagccattct cagttcggac tgtaggctgc aactagcata   1320
cacgaagtcg gaatcgctag taatcgcgga tcagcacgcc gcggtgaata cgttcccggg   1380
ccttgtacac accgcccgtc acaccatgag agtttgtaac acccgaagcc ggtggcgtaa   1440
cccttttagg gagcgagccg tctaagggtg gacaaaatag gctacctacc t            1491

<210> SEQ ID NO 15
<211> LENGTH: 1481
<212> TYPE: DNA
<213> ORGANISM: Lactobacillus brevis

<400> SEQUENCE: 15
taggaactgg ggcatgccta tactgcaagt cgaacgagct tccgttgaat gacgtgcttg     60
cactgatttc aacaatgaag cgagtggcga actggtgagt aacacgtggt ggaatctgcc    120
cagaagcagg ggataacact tggaaacagg tgctaatacc gtataacaac aaaatccgca    180
tggattttgt ttgaaaggtg gcttcggcta tcacttctgg atgatcccac tgcgtattag    240
ttagttggtg aggtaaaggc ccaccaagac gatgatacgt agccgacctg agagggtaat    300
cggccacatt gggactgaga cacggcccaa actcctacgg gaggcagcag tagggaatct    360
tccacaatgg acgaaagtct gatggagcaa tgccgcgtga gtgaagaagg gtttcggctc    420
gtaaaactct gttgttaaag aagaacaccct tgagagtaa ctgttgaggg gttgagggta    480
tttaaccaga aagccacggc taactacgtg ccagcagccg cggtaatacg taggtggcaa    540
tcgttgtccg gatttattgg gcgtaaagcg agcgcaggcg gttttttaag tctgatgtga    600
aagccttcgg cttaaccgga gaagtgcatc ggaaactggg agacttgagt gcagaagagg    660
acagtggaac tccatgtgta gcggtggaat gcgtagatat atggaagaac accagtggcg    720
aaggcggctg tctagtctgt aactgacgct gaggctcgaa agcatgggta gcgaacagga    780
ttagataccc tggtagtcca tgccgtaaac gatgagtgct aagtgttgga gggtttccct    840
ccttcagtgc tgcagctaat gcgataagca actccgcctg ggagtacga ccgcaaggtt    900 gaaaactcaa aggaattgac gggggcccgc acaagcggtg gagcatgtgg tttaattcga    960
agctacgcga agaaccttac caggtcttga catcttctgc caatcttaga gataagacgt   1020
```

-continued

```
tcccttcggg dacagaatga caggtggtgc atggttgtcg tcagctcgtg tcgtgagatg   1080
ttgggttaag tcccgcaacg agcgcaaccc ttattatcag ttgccagcat tcagttgggc   1140
actctggtga gactgccggt gacaaaccgg aggaaggtgg ggatgacgtc aaatcatcat   1200
gccccttatg acctgggcta cacacgtgct acaatggacg gtacaacgag tcgcgaagtc   1260
gtgaggctaa gctaatctct taaagccgtt ctcagttcgg attgtaggct gcaactcgcc   1320
tacatgaagt tggaatcgct agtaatcgcg gatcagcatg ccgcggtgaa tacgttcccg   1380
ggccttgtac acaccgcccg tcacaccatg agagtttgta acacccaaag ccggtgagat   1440
aaccttcggg agtcagccgt ctaaggtgga cagagatagg g                      1481
```

<210> SEQ ID NO 16
<211> LENGTH: 1456
<212> TYPE: DNA
<213> ORGANISM: Leuconostoc citreum

<400> SEQUENCE: 16

```
ggcgtgccta atacatgcaa gtcgaacgcg cagcgagagg tgcttgcacc tttcaagcga    60
gtggcgaacg ggtgagtaac acgtggataa cctgcctcaa agcgtggaga taacatttgg   120
aaacagatgc taataccgaa taaaacttag tatcgcatga tatcaagtta aaaggcgcta   180
cggcgtcacc tagagatgga tccgcggtgc attagttagt tggtggggta aaggcttacc   240
aagacgatga tgcatagccg agttgagaga ctgatcggcc acattgggac tgagacacgg   300
cccaaactcc tacgggaggc tgcagtaggg aatcttccac aatgggcgca agcctgatgg   360
agcaacgccg cgtgtgtgat gaaggctttc gggtcgtaaa gcactgttgt atgggaagaa   420
atgctaaaat agggaatgat tttagtttga cggtaccata ccagaaaggg acggctaaat   480
acgtgccagc agccgcggta atacgtatgt cccgagcgtt atccggattt attgggcgta   540
aagcgagcgc agacggttga ttaagtctga tgtgaaagcc cggagctcaa ctccggagtg   600
gcattgaaaa ctggggaact tgagtgtctg tagaggtcag aggaactcca tgtgtagcgg   660
tgaaatgcgt agatatatgg aagaacacca gtggcgaagg cggcttactg gacaacaact   720
gacgttgagg ctcgaaagtg tgggtagcaa acaggattag ataccctggt agtccacacc   780
gtaaacgatg aatactaggt gttaggaggt ttccgcctct tagtgccgaa gctaacgcat   840
taagtattcc gcctggggag tacgaccgca aggttgaaac tcaaaggaat tgacggggac   900
ccgcacaagc ggtggagcat gtggtttaat tcgaagcaac gcgaagaacc ttaccaggtc   960
ttgacatcct ttgaagcttt tagagataga agtgtgctct tcggagccaa agtgacaggt  1020
ggtgcatggt ggtcgtcagc tcgtgtcgtg agatgttggg ttaagtcccg caaggagcgc  1080
aacccttatt gttagttgcc agcattcagt tgggcactct agcgagactg ccggtgacaa  1140
accggaggaa ggcggggacg acgtcagatc atcatgcccc ttatgacctg gctacacac   1200 gtgctacaat ggcgtataca acgagttgcc aacctgcgaa ggtgagctaa tctcttaaag  1260
tacgtctcag ttcggactgc agtctgcaac tcgactgcac gaagtcggaa tcgctagtaa  1320
tcgcggatca gcacgccgcg gtgaatacgt tcccgggtct gtacacacc gcccgtcaca  1380 ccatgggagt ttgaacgccc aaagtccggt ggcctaacct tcgggaggca gcctctaagg  1440
ctgccgaatg ggaaaa                                                 1456
```

<210> SEQ ID NO 17
<211> LENGTH: 1455
<212> TYPE: DNA
<213> ORGANISM: Carnobacterium maltaromaticum

<400> SEQUENCE: 17

```
ggggaatggc ggcgtgctat acatgcagtc gaacgcacga agttgaagag cttgctcttt     60
accaagtgag tggcggacgg gtgagtaaca cgtgggtaac ctgcccatta gaggggata     120
acattcggaa acggatgcta ataccgcata gtttcaggaa tcgcatgatt cttgaaggaa    180
aggtggcttc ggctaccact aatggatgga cccgcggcgt attagctagt tggtgaggta    240
atggctcacc aaggcaatga tacgtagccg acctgagagg gtgatcggcc acactgggac    300
tgagacacgg cccagactcc tacgggaggc agcagtaggg aatcttccgc aatggacgaa    360
agtctgacgg agcaacgccg cgtgagtgaa gaaggttttc ggatcgtaaa actctgttgt    420
taaagaagaa caaggatgag agtaactgct catccctga cggtatttaa ccagaaagcc     480
acggctaact acgtgccagc agccgcggta atacgtaggg ggcaagcgtt gtccggattt    540
attgggcgta aagcgagcgc aggcggttct ttaagtctga tgtgaaagcc cccggctcaa    600
ccggggaggg tcattggaaa ctggagaact tgagtgcaga agaggagagt ggaattccac    660
gtgtagcggt gaaatgcgta gatatgtgga ggaacaccag tggcgaaggc gactctctgg    720
tctgtaactg acgctgaggc tcgaaagcgt ggggagcaaa caggattaga tacctggta    780
gtccacgccg taaacgatga gtgctaagtg ttggagggtt tccgcccttc agtgctgcag    840
ctaacgcatt aagcactccg cctgggagt acggccgcaa ggctgaaact caaggaatt     900
gacgggggacc cgcacaagcg gtggagcatg tggtttaatt cgaagcaacg cgaagaacct   960
taccaggtct tgacatcctt tgaccactct agagatagag ctttcccttc ggggacaaag   1020
tgacaggtgg tgcatggttg tcgtcagctc gtgtcgtgag atgttgggtt aagtcccgca   1080
acgagcgcaa cccttattac tagttgccag catttagttg ggcactctag tgagactgcc   1140
ggtgacaaac cggaggaagg tggggatgac gtcaaatcat catgccctt atgacctggg    1200
ctacacacgt gctacaatgg atggtacaac gagtcgcaag gtcgcgaggc caagctaatc   1260
tcttaaagcc attctcagtt cggattgtag gctgcaactc gcctacatga agccggaatc   1320
gctagtaatc gcggatcaga acgccgcggt gaatacgttc ccgggtcttg tacacaccgc   1380
ccgtcacacc acgagagttt gtaacacccg aagccggtga ggtaaccttt taggagccca   1440
gccgtctaag gggaa                                                    1455
```